(12) United States Patent
Bard

(10) Patent No.: US 6,210,967 B1
(45) Date of Patent: Apr. 3, 2001

(54) DNA ENCODING A MAMMALIAN LPA RECEPTOR AND USES THEREOF

(75) Inventor: Jonathan A. Bard, Doylestown, PA (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

(21) Appl. No.: 08/987,943

(22) Filed: Dec. 10, 1997

(51) Int. Cl.[7] .............................. C12N 5/10; C12N 15/12
(52) U.S. Cl. .................. 435/361; 435/252.3; 435/320.1; 435/325; 435/348; 435/356; 435/357; 435/365; 435/366; 530/350; 536/23.5; 536/24.31
(58) Field of Search ............................... 536/23.5, 24.31; 435/252.3, 320.1, 69.1, 361; 530/350

(56) References Cited

PUBLICATIONS

An et al, Molecular Cloning or the Human Edge2 Protein and its Identification as a Functional Cellular Receptor for Lysophphatidic Acid. Biochem. Biophys. Res. Commun. vol. 231, No. 3, pp. 619–622. see entire article, Feb. 1997.*
Hecht et al. Ventricular Zone Gene–1 (vzg–1) Encodes a Lysophosphatidic Acid Receptor Expressed in Neurogenic Regions of the Developning Cerebral Cortex. J. Cell Biol. vol. 135, No. 4, pp. 1071–1083, see entire article, Nov. 1996.*
Johnson et al, GenEmbl database, Accession Nos: L06281, M26719. Drosophila pseudoobscura (tissue library:Charon 4 and EMBL4) adult DNA, Dec. 1994.*
Gibert et al, GenEmbl data base, Accession No. U73043. Bos taurus Dlb dopamine receptor gene, partial cds. Direct submission, Oct. 1996.*
Wang et al, GenEmbl database, Accession No. U15158. Oryctolagus cuniculus ESP–2 (esp–2) mRNA, partial cds, Oct. 1995.*
Genbank Accession #U92642, published Jan. 1, 1998 (Exhibit 2).
Genbank Accession #U76385, published Dec. 3, 1996 (Exhibit 3).

An, S., et al., Molecular Cloning of the Human Edg2 Protein and its Identification as a Functional Cellular Receptor for Lysophosphatidic acid. Biochem. Biophys. Res. Commun. Feb. 1997; 231(3): 619–622 (Exhibit 2).
Hetch, J.H., et al., Ventricular Zone Gene–1 (vzg–1) Encodes a Lysophosphatidic Acid Receptor Expressed in Neurogenic Regions of the Developing Cerebral Cortex. J. Cell Biol. Nov. 1996; 135(4): 1071–1081 (Exhibit 3).
Thomson, F.J., et al., Identification and Characterization of a Lysophosphatidic Acid Receptor. Molecular Pharmacology. 1994; 45(4): 718–723 (Exhibit 4).
Guo, A., et al., "Molecular Cloning Of A High–Affinity Receptor For The Growth Factor–Like Lipid Mediator Lysophosphatidic Acid Form Zenopus Oocytes," *Proc. Natl. Acad. Sci.* USA (1996) 93: 14367–14372 (Exhibit 2);.
Moolenaar, W.H., "Lysophosphatidic Acid, a Multifunctional Phospholipid Messenger," *J. Biol. Chem.* (1995) 270(22): 12949–12952 (Exhibit 3); and.
Moolenaar, W.H., "LPA: A Novel Lipid Mediator With Diverse Biological Actions," *Trends in Cell Biology* (1994) 4: 213–219 (Exhibit 4).

* cited by examiner

*Primary Examiner*—Gary L. Kunz
*Assistant Examiner*—Eileen B. O'Hara
(74) *Attorney, Agent, or Firm*—John P. White; Cooper & Dunham LLP

(57) ABSTRACT

This invention provides an isolated nucleic acid encoding a mammalian LPA receptor, a purified mammalian LPA receptor, vectors comprising isolated nucleic acid encoding an mammalian LPA receptor, cells comprising such vectors, antibodies directed to a mammalian LPA receptor, nucleic acid probes useful for detecting nucleic acid encoding a mammalian LPA receptor, antisense oligonucleotides complementary to unique sequences of nucleic acid encoding mammalian LPA receptor, transgenic, nonhuman animals which express DNA encoding a normal or a mutant mammalian LPA receptor, methods of isolating an mammalian LPA receptor, methods of treating an abnormality that is linked to the activity of the mammalian LPA receptor, as well as methods of determining binding of compounds to mammalian LPA receptors.

21 Claims, 11 Drawing Sheets

FIGURE 1A

```
  1  GGAATTCTAGAAAACACCTGTAAAGCTTAAACGCGTGCTTTCTTCAACGCGTTTGGAAACT   60
 61  CTAACCCCTTCTCTTTTGTACTTTTGCTTGCTGTCCACTACAGAGGGTCCAAGCACGAA    120
121  GCTGTGCACAGAGTCGCTCTCCACAGAGATGCTTAGGATGTGATCCATGAATCGCAAATC   180
181  CCAGCTAGTGCTCACAAAGACGGACATTTCTCCCCAAGACCATTCCAGTGCCCCAGAGGT   240
241  CCACAGACATCCAGGAAGATGCAGCCAGCAGACAAAGAATGGCAGCCACCCAAGTGCTGA   300
301  GGGGAGCCCTCCCGGCCATTTCTGTCCCAGCTCTCTCCAAGGGTCTCTCCACGATGCCTGCAA   360
361  CAGCACGTCCCTTGAGGCTTACACATACCTGCTGAACACCAGCAACGCCTCAGACTC     420
421  GGGGTCCACCCAGTTGCCCGCACCCCTCAGGATCTCCTTGGCCATAGTGATGCTGCTGAT   480
481  GACCGTGGTGGGGTTCCTGGGCAACACTGTGGTCTGCATCATCGTGTACCAGAGGCCGGC   540
541  TATGCGCTCGGCCATCAACCTGCTGCTGGCCACCCTGGCCTTCTCCGACATCATGCTGTC   600
601  CCTCTGCTGCATGCCCTTCACCGCCGTCCACCCTCATCACCGTGCGCTGGCACTTTGGGGA   660
661  CCACTTCTGCCGCCTCTCAGCCACGCTCTACTGGTTTTTTGTCCTGGAGGCGTGGCCAT    720
721  CCTGCTCATCATCAGCGTGGACCGCTTCCTCATCATCGTCCAGCGCCAGGACAAGCTGAA   780
781  CCCGCGCAGGGCCAAGGTGATCATCGCGGTCTCCTGGGTGCTGTCCTTCTGCATCGCGGG   840
```

FIGURE 1B

```
 841  GCCCTCGCTCACGGGCTGGACGCTGGTGAGGTGCCGGGCGGGCCCCACAGTGCCGTGCT   900
 901  GGGCTACACGGAGCTCCCGCTGACCGCGCTACGTGGTCACCTTGGTGGTGGCCGTGTT    960
 961  CTTCGCGCCCTTTGGCGTCATGCTGTGCGCCTACATGTCATCCTCAACACGGTCCGCAA  1020
1021  GAAGGCCGTGCGCGTGCACAACCAGTCGGACAGCCTGGACCTGGCAGCTCACCAGGGC   1080
1081  GGGCCTGCGCGCTGCAGCGGCAGCAACAGGTCAGCGTGGACTTGAGCTTCAAGACCAA   1140
1141  GGCCTTCACCACCATCCTGATCCTCTGTGGGCTTCTCCCTCTGCTGCCCCACTC       1200
1201  CGTCTACAGCCTCCTGTCTGTGTTAGCCAGCGCTTTTACTGCGGTTCCTCCTTCTACGC  1260
1261  CACCAGCACCTGCGTCCTCAGTACCTCAAGTCCGTCTCTTCAACCCCATCGTCTA      1320
1321  CTGCTGGAGAATCAAAAAATTCCGCGAGGCCTGCATAGAGTTGCTGCCCCAGACCTTCCA 1380
1381  AATCCTCCCCAAAGTGCCTGAGCGGATCCGAAGGAGAATCCAGCCAAGCACAGTCTACGT 1440
1441  GTGCAATGAAAACCAGTCTGCGGTTTAGGGGTCAGGGGCCACAGAGAAGGGGCAGCTG   1500
1501  AGCCCCAGTCCCAGGGTGGATCTGTCCTGCTCTGTTCCCTGGCATGTTGGTCATAGTCTG 1560
1561  CACTTTGTGTGGCAATTTAAGCACAAAGGTACTCATTTGTAATCAGATGAGCTGCAGCT  1620
1621  CCCAAATTTCAAATTTTGGCACGATGAATTATTTTGTTTCTCTTTGCAGAGAGCCAAAT  1680
```

FIGURE 1C

1681 ATGGGGCTGATGGGAACTGCAACGTCATTAAGTCAAAAATGGAGTGGGCTGGGGAGTGCA 1740

1741 GAAGTTGGGCAGAAA 1755

FIGURE 2A

```
  1  ATGGCCTGCAACAGCACGTCCCTTGAGGCTTACACATACCTGCTGCTGAACACCAGCAAC   60
 61  GCCTCAGACTCGGGGTCCACCCAGTTGCCCGCACCCCTCAGGATCTCCTTGGCCATAGTG  120
121  ATGCTGCTGATGACCGTGTGGGTTCCTGGCAACACTGTGGTCTGCATCATCGTGTAC     180
181  CAGAGGCCGGCTATGCGCTCGGCCATCAACCTGCTGCTGGCCACCCTGGCCTTTCCGAC   240
241  ATCATGCTGTCCCCTCTGCTGCATGCCCCTTCACCGCCGTCACCCTCATCACCGTGCTGG  300
301  CACTTTGGGACCACTTCTGCCGCTCTCTCAGCCACGCTGGACCGCTTCCTCATCATCGTC  360
361  GGCGTGGCCATCCTGCTCATCATCAGCGTGGACCGCTTCCTCATCATCGTCCAGCGCCAG  420
421  GACAAGCTGAACCCGCGCAGGGCCAAGGTGATCATCGCGGTCTCCTGGGTGCTGTCCTTC  480
481  TGCATCGCGGGGCCCTCGCTCACGGGCTGGTGGTGAGGTGCCGGGCGCGGGGCCCCA     540
541  CAGTGCCGTGCTGGCTACACGGAGCTCCCCCGCTGACCGCCTACGTGGTCACCTTGGTG  600
601  GTGGCCCGTGTTCTTCGCGCCCTTTGGCGCCGTCATGCTGTGCGCCTACATGTGCATCCTCAAC  660
661  ACGGTCCGCAAGAAGGCCGTGCGCGTGCACAACCAGTCGGACAGCCTGGACCTGCGGCAG  720
721  CTCACCAGGGCGGCCTGCAGCGGGCAACAGGTCAGCGTGACTTGAGC              780
781  TTCAAGACCAAGGCCTTCACCACCATCCTGATCCTCTTCGTGGGCTTCCTCCTCTGCTGG  840
```

FIGURE 2B

```
841   CTGCCCCACTCCGTCTACAGCCTCCTGTCTGTGTTTAGCCAGCGCTTTTACTGCGGTTCC   900
901   TCCTTCTACGCCACCAGCACCTGCGTCCTGTGGCTCAGTTACCTCAAGTCCGTCTTCAAC   960
961   CCCATCGTCTACTGCTGGAGAATCAAAAAATTCCGGAGGCCTGCATAGAGTTGCTGCCC   1020
1021  CAGACCTTCCAAATCCTCCCCAAAGTGCCTGAGCGGATCCGAAGGAGAATCCAGCCAAGC  1080
1081  ACAGTCTACGTGTGCAATGAAAACCAGTCTGCGGTTTAG                       1119
```

FIGURE 3A

```
1    M A C N S T S L E A Y T Y L L L N T S N    20
21   A S D S G S T Q L P A P L R I S L A I V    40
                                   |_____|
                                        I
41   M L L M T V V G F L G N T V V C I I V Y    60
61   Q R P A M R S A I N L L L A T L A F S D    80
         |_____|
                        II
81   I M L S L C C M P F T A V T L I T V R W    100
101  H F G D H F C R L S A T L Y W F F V L E    120
                         |_____|
                                 III
121  G V A I L L I I S V D R F L I I V Q R Q    140
                                     |_____|
                                        IV
141  D K L N P R R A K V I I A V S W V L S F    160
     |_____|
161  C I A G P S L T G W T L V E V P A R A P    180
```

FIGURE 3B

```
181  Q C V L G Y T E L P A D R A Y V V T L V              200
            ├─V────────────────
201  V A V F F A P F G V M L C A Y M C I L N              220
221  T V R K K A V R V H N Q S D S L D L R Q              240
241  L T R A G L R R L Q R Q Q Q V S V D L S              260
                                    ├─VI──────
261  F K T K A F T T I L I L F V G F S L C W              280
                ├──────────────
281  L P H S V Y S L L S V F S Q R F Y C G S              300
                              ├─VII─────────
301  S F Y A T S T C V L W L S Y L K S V F N              320
321  P I V Y C W R I K K F R E A C I E L L P              340
341  Q T F Q I L P K V P E R I R R I Q P S                360
361  T V Y V C N E N Q S A V                              372
```

FIGURE 4A

```
1   ATGGCCTGCAACAGCACGTCCCTTGAGGCTTAcaCATACCTGCTGCTGAA  50
        ||||||||||||  ||| |||| |  ||| |||| ||| |  |||
1   ATGGGCTGCAATATACTGCCCTAGACAATTGCATGCTTCCCAATCTCAG  50

51  CACCAGCAACGCCTCAGACTCGGGGTCCACCCAGTTGCCCGCACCCCTCA  100
    |||||  |||  || ||||| |||| ||||||||||   ||||| |||||
51  CATTGCTACTGCTCCTCTAGACTTGAGGTTTGCATTTTCCACCCACTCA  100

101 GGATCTCCTTGGCCATAGTGATGCTGCTGATGACCGTGGTGGGGTTCCTG  150
    ||| | ||||||||| |||||  ||||||||| |||| | ||| ||| |
101 GGATGTGTTGGCAATAGTTTTGCCTTATTGTTTATCAGAATGATGCGTTC  150

151 GGCAACACTGTGGTCTGCATCATCGTGTACCAGAGGCCGGCTATGCGCTC  200
    |||||  |||||  | |||| || |||||   ||||||||||||||||
151 GGCAATGCAATAGTTTGCCTTATTGTTTATCAGAAGCCAGCCATGCGTTC  200

201 GGCCATCAACCTGCTGCTGGCCACCCTGGCCTTCTCCGACATCATGCTGT  250
    ||||||||| | ||||| |||||| ||||| |||||||||||||| |||
201 AGCAATCAATCTTCTCCTAGCAACACTGGCCATTCTGACATCATGTTGT  250

251 CCCTCTGCTGCATGCCCTTCACCGCCGTCATCCCTCATCACCGTgCGCTGG  300
    |||| | |||||||||| |||| ||||  | |||||||||||| ||||||
251 CCCTTTCTGTATGCCCTTTACCGCAGTAACAATAATAACTGGGAGCTGG  300
```

FIGURE 4B

```
301 CACTTTGGGGACCACTTCTGCCGCCTCTCAGCCACGCTCTACTGGTTTTT 350
    |||  ||||| ||| ||||||| || ||||||||| |||||||||||||
301 CTCTTTGAACTCAGTTTTGCCAGATATCAGCCATGCTGTACTGGTTTTT 350

351 TGTCCTGGAGGGCGTGGCCATCCTGCTCATCATCAGCGGTGGACCGCTTCC 400
    ||| |||| |||||||||||| || ||||| ||||||||||| |||||||
351 TGTGTTAGAAGGCGTGGCCATTCTACTTCATCATCAGCGTGGATCGTTTCC 400

401 TCATCATCGTCCAGCGCCAGGACAAGCTGAACCCGGCAGGGCCAAGGTG 450
    |||||| |||||||||||||||||| |||||||||||  |||||||| |
401 TTATTATTGTACAGAGGCAGGACAAACTGAACCCACATCCGGGCCAAGATC 450

451 ATCATCGCGGTCTCCTGGGTGCTCCTTCTGCATCGCGGGCCCTCGCT 500
    |||||||||||| ||||||||| |||| ||||||| ||||| ||||| ||
451 ATGATTGCTGCTTCTTGGGTACTGTCTCTTTTTGTATCGTCTTTACCGTCGGT 500

501 CACGGGCTGGACGCTGGTGGAGGTGCCGGCCCCACAGTGCCTGC 550
    ||||||||||||| |||| |||||||| |||||| ||||||| ||
501 GGTTGGGTGGACGTTAGTGGAGGTGCCTCCACACGTGCTCCACAGTGTGTTC 550

551 TGGGCTACACGGAGCTCCCCGCTGACCGCGCTGGTCACCTTGGTG 600
    ||||||||| ||||| |||||||| || || ||| ||| || |||
551 TCGGTTATACAGAATTTTCTGCTGACAGAGTTTATGCAGTCATGCTCATA 600
```

FIGURE 4C

```
601 GTGGCCGTGTTCTTCGGCCCCTTTGGCGTCATGCTGTGCGCCTACATGTG  650
    |||  ||||| ||||| |||||| ||||| ||||||||||| ||||||||
601 GTAGCAGTCTTCTTCATTCCATTCAGTGTAATGTTGTACTCGTATTTGTG  650

651 CATCCTCAACACGGTCCGCAAGAAGGCCGTGCGCGTGCACAACCAGTCGG  700
    ||||||||||| ||||||||  ||||| ||||| || ||||||||| ||
651 TATCCTGAACACCGTTAGAAGAAATGCTGTGTCAGAATTCACACTCATGCCG  700

701 ACAGCCTGGACTGCGCAGCTCCTGCGCGGCGCAGCTCACCAGGCGCCTGCAG  750
     ||||| ||| || ||||||  ||||  ||||||  ||||| |  ||||||
701 ACAGCTTGTGTCTCAGCCAAGTAAGCAAATTGGGACTTATGGGACTTCAG  750

751 CGGCAGCAACAGGTCAGCCGTGGACTTGAGCTTCAAGACCAAGGCCTTCAC  800
    ||||| |||||  || || |||| ||||||||  ||| |  ||||||||||
751 AGGCCACCACCAAATGAATGTGGACATGAGTTTCAAAACCAGGGCCTTCAC  800

801 CACCATCCCTGATCCCTCTTCGTGGGCTTCCTCCCTGCTGCCCCACT  850
    ||||| || | |||| ||| |||||| | ||| || |||||| |||
801 CACTATTTTGATTCCTCATTGGGTTTTCACTCTGCTTCCTCACT  850

851 CCGTCTACAGCCCTCCTGTGTGTTTAGCCAGCGCTTTACTGCGGTTCC  900
      |||||||| || ||| |||| ||| | ||| |||||| || |
851 CAGTATTCAGCTTACTTTCAGTATTCAGGACATTTACTACAGCTCT  900
```

FIGURE 4D

```
901  TCCTTCTACGGCCACCAGCACCTGGCGTCCTGTGTGGCTCAGTTACCTCAAGTC  950
      ||| ||| || ||  |||||| | |  ||||| |||||||||||| |||| ||
901  TCATTTACAGCATCAGCACGTGTACCTTGTGGCTCACTTACCTGAAGTC  950

951  CGTCTTCAACCCCATCGTCTACTGCTGGAGAATCAAAAATTCCGGAGG  1000
      |||||||||| || ||||||  ||||| |||||| ||  || |||||
951  TGTCTTCAACCCCTGTTATATTGCTGGAGGATCAAGAAGTTCCGTGAGG  1000

1001 CCTGCATAGAGTTGCTGCTGCCCCCAGACCCTTCCAAATCCCCCCAAAGTGCCT  1050
      ||||| || |||| |||| | || ||||||||||| | ||  |||| ||
1001 CCTGTCTGGAGTTCATGCCCAAGATCCTTCCAAATGTACGA  1050

1051 GAGCGGGATCCGAAGGAGAATCCAGCCACAGTCTACGTGTGCAATGA  1100
      ||  || ||| ||| ||||| | ||||||| |||| ||| ||| ||
1051 GGAAGGACAAGACGCGGATTCGTCCAAGCACAATTTATGTGTGTGGGGA  1100

1101 AAACCAGTCTGCGGTTTAG  1119
      || ||||| || ||| ||
1101 ACATCAGTCAGCTGTTTAA  1119
```

DNA ENCODING A MAMMALIAN LPA RECEPTOR AND USES THEREOF

BACKGROUND OF THE INVENTION

Throughout this application, various publications are referenced in parentheses by author and year. Full citations for these references may be found at the end of the specification immediately preceding the sequence listings and the claims. The disclosure of these publications in their entireties are hereby incorporated by reference into this application to describe more fully the art to which this invention pertains.

Biologically active phospholipids are emerging as important intracellular signaling molecules. Among these, lysophosphatidic acid (LPA; 1-acyl-glycerol-3-phosphate) is the simplest glycerophospholipid (Moolenaar, 1994). LPA produces a wide variety of biological responses such as induction of cell proliferation, stimulation of neurite retraction, platelet aggregation, smooth muscle contraction, tumor cell invasion, neurotransmitter release, chloride efflux and chemotaxis (Moolenaar, 1994; Jalink et al., 1994; Van Corven et al., 1989; Tigyi et al., 1994; Tigyi and Miledi, 1992; Jalink et al., 1993; Tokumura et al., 1994; Piazza et al., 1995). LPA is the product of the blood-clotting process and is therefore present in serum. LPA derived from platelets appears to be an important mediator of wound healing and tissue regeneration (Moolenaar, 1995).

The known effects of LPA appear to be mediated by G protein-coupled receptor(s). Specific LPA binding sites have been demonstrated in membranes from 3T3 cells and rat brain with Kd values in the low nanomolar range (Thomson et al., 1994). The actions of LPA are mediated by at least four G protein-mediated signaling pathways: stimulation of phospholipase C and phospholipase D, inhibition of adenylyl cyclase, activation of Ras and Raf/MAP kinase pathway, and tyrosine phosphorylation of focal adhesion proteins (Moolenaar, 1995).

We describe here the isolation and characterization of a novel mammalian LPA receptor, specifically a human LPA receptor. This receptor can serve as a tool for the drug design of novel therapeutic agents for various indications, including cancer (preferably tumor reduction or prevention), platelet aggregation (as an anti-coagulant), vascular restenosis, arthritis (as an anti-inflammatory), wound healing, tissue regeneration (preferably skin and nerve regeneration), blood coagulation, osteoporosis (bone regeneration), and cosmetic uses (preferably the prevention of abnormal growths or scarring or for augmentation).

Independently, the identification of a complementary DNA from Xenopus that encodes a functional high-affinity receptor for LPA has recently been reported (Guo, et al., 1996). Analysis of this receptor revealed that it is a G-protein-coupled-receptor.

SUMMARY OF THE INVENTION

This invention provides an isolated nucleic acid encoding a mammalian LPA receptor. In an embodiment, the mammalian LPA receptor is a human LPA receptor.

This invention provides a purified mammalian LPA receptor protein.

This invention provides a vector comprising a nucleic acid encoding a mammalian LPA receptor. This invention also provides for a vector comprising a nucleic acid encoding a human LPA receptor. Such a vector may be adapted for expression of the mammalian LPA receptor in mammalian or non-mammalian cells.

This invention provides a plasmid designated HL-18a (ATCC Accession No. 209448). This invention also provides a membrane preparation isolated from the cells.

This invention provides a nucleic acid probe comprising at least 15 nucleotides, which probe specifically hybridizes with a nucleic acid encoding a mammalian LPA receptor, wherein the probe has a unique sequence corresponding to a sequence present within one of the two strands of the nucleic acid which encode the mammalian LPA receptor contained in plasmid HL-18a (ATCC Accession No. 209448).

This invention also provides a nucleic acid probe comprising at least 15 nucleotides, which probe specifically hybridizes with a nucleic acid encoding a mammalian LPA receptor, wherein the probe has a unique sequence corresponding to a sequence present within (a) the nucleic acid sequence of shown in FIG. 2 (Seq. I.D. No. 2) or (b) the reverse complement thereto.

This invention provides a nucleic acid probe comprising a nucleic acid molecule of at least 15 nucleotides which is complementary to a unique fragment of the sequence of a nucleic acid molecule encoding a mammalian LPA receptor.

This invention provides a nucleic acid probe comprising a nucleic acid molecule of at least 15 nucleotides which is complementary to the antisense sequence of a unique fragment of the sequence of a nucleic acid molecule encoding a mammalian LPA receptor.

This invention provides an antisense oligonucleotide having a sequence capable of specifically hybridizing to the RNA of the mammalian LPA receptor, so as to prevent translation of the RNA. This invention also provides an antisense oligonucleotide having a sequence capable of specifically hybridizing to the genomic DNA encoding a mammalian LPA receptor.

This invention further provides an antibody capable of binding to a mammalian LPA receptor. This invention also provides for an antibody capable of competitively inhibiting the binding of the antibody to a mammalian LPA receptor.

This invention provides a pharmaceutical composition comprising (a) an amount of the oligonucleotide capable of passing through a cell membrane and effective to reduce expression of a mammalian LPA receptor and (b) a pharmaceutically acceptable carrier capable of passing through a cell membrane.

This invention provides a transgenic, nonhuman mammal expressing DNA encoding a mammalian LPA receptor. This invention also provides a transgenic, nonhuman mammal comprising a homologous recombination knockout of the native mammalian LPA receptor. This invention further provides a transgenic, nonhuman mammal whose genome comprises antisense DNA complementary to DNA encoding a mammalian LPA receptor so placed within the genome as to be transcribed into antisense mRNA which is complementary to mRNA encoding a mammalian LPA receptor and which hybridizes to mRNA encoding a mammalian LPA receptor, thereby reducing its translation.

This invention provides for a process for identifying a chemical compound which specifically binds to a mammalian LPA receptor which comprises contacting cells containing DNA encoding and expressing on their cell surface the mammalian LPA receptor, wherein such cells do not normally express the mammalian LPA receptor, with the compound under conditions suitable for binding, and detecting specific binding of the chemical compound to the mammalian LPA receptor.

This invention provides for a process for identifying a chemical compound which specifically binds to a mammalian LPA receptor which comprises contacting a membrane fragment from a cell extract of cells containing DNA encoding and expressing on their cell surface the mammalian LPA receptor, wherein such cells do not normally express the mammalian LPA receptor, with the compound under conditions suitable for binding, and detecting specific binding of the chemical compound to the mammalian LPA receptor.

This invention provides for a process involving competitive binding for identifying a chemical compound which specifically binds to a mammalian LPA receptor which comprises separately contacting cells expressing on their cell surface the mammalian LPA receptor, wherein such cells do not normally express the mammalian LPA receptor, with both the chemical compound and a second chemical compound known to bind to the receptor, and with only the second chemical compound, under conditions suitable for binding of both compounds, and detecting specific binding of the chemical compound to the mammalian LPA receptor, a decrease in the binding of the second chemical compound to the mammalian LPA receptor in the presence of the chemical compound indicating that the chemical compound binds to the mammalian LPA receptor.

This invention provides for a process involving competitive binding for identifying a chemical compound which specifically binds to a mammalian LPA receptor which comprises separately contacting a membrane fraction from a cell extract of cells expressing on their cell surface the mammalian LPA receptor, wherein such cells do not normally express the mammalian LPA receptor, with both the chemical compound and a second chemical compound known to bind to the receptor, and with only the second chemical compound, under conditions suitable for binding of both compounds, and detecting specific binding of the chemical compound to the mammalian LPA receptor, a decrease in the binding of the second chemical compound to the mammalian LPA receptor in the presence of the chemical compound indicating that the chemical compound binds to the mammalian LPA receptor.

This invention provides for a method of screening a plurality of chemical compounds not known to bind to a mammalian LPA receptor to identify a compound which specifically binds to the mammalian LPA receptor, which comprises (a) contacting cells transfected with and expressing DNA encoding the mammalian LPA receptor with a compound known to bind specifically to the mammalian LPA receptor; (b) contacting the preparation of step (a) with the plurality of compounds not known to bind specifically to the mammalian LPA receptor, under conditions permitting binding of compounds known to bind the mammalian LPA receptor; (c) determining whether the binding of the compound known to bind to the mammalian LPA receptor is reduced in the presence of the compounds within the plurality of compounds, relative to the binding of the compound in the absence of the plurality of compounds; and if so, (d) separately determining the binding to the mammalian LPA receptor of compounds, so as to thereby identify the compound which specifically binds to the mammalian LPA receptor.

This invention provides for a method of screening a plurality of chemical compounds not known to bind to a mammalian LPA receptor to identify a compound which specifically binds to the mammalian LPA receptor, which comprises (a) preparing a cell extract from cells transfected with and expressing DNA encoding the mammalian LPA receptor, isolating a membrane fraction from the cell extract, contacting the membrane fraction with a compound known to bind specifically to the mammalian LPA receptor; (b) contacting the preparation of step (a) with the plurality of compounds not known to bind specifically to the mammalian LPA receptor, under conditions permitting binding of compounds known to bind the receptor; (c) determining whether the binding of the compound known to bind to the mammalian LPA receptor is reduced in the presence of the compounds within the plurality of compounds, relative to the binding of the compound in the absence of the plurality of compounds; and if so (d) separately determining the binding to the mammalian LPA receptor of compounds included in the plurality of compounds, so as to thereby identify the compound which specifically binds to the mammalian LPA receptor.

This invention provides for a method of detecting expression of a mammalian LPA receptor by detecting the presence of mRNA coding for the mammalian LPA receptor which comprises obtaining total mRNA from the cell and contacting the mRNA so obtained from the nucleic acid probe under hybridizing conditions, detecting the presence of mRNA hybridizing to the probe, and thereby detecting the expression of the mammalian LPA receptor by the cell.

This invention provides for a method of detecting the presence of a mammalian LPA receptor on the surface of a cell which comprises contacting the cell with the antibody under conditions permitting binding of the antibody to the receptor, detecting the presence of the antibody bound to the cell, and thereby detecting the presence of a mammalian LPA receptor on the surface of the cell.

This invention provides for a method of determining the physiological effects of varying levels of activity of mammalian LPA receptors which comprises producing a transgenic, nonhuman mammal whose levels of mammalian LPA receptor activity are varied by use of an inducible promoter which regulates mammalian LPA receptor expression.

This invention provides for a method of determining the physiological effects of varying levels of activity of mammalian LPA receptors which comprises producing a panel of transgenic, nonhuman mammals each expressing a different amount of mammalian LPA receptor.

This invention provides for a method for identifying an antagonist capable of alleviating an abnormality wherein the abnormality is alleviated by decreasing the activity of a mammalian LPA receptor comprising administering a compound to a transgenic, nonhuman mammal, and determining whether the compound alleviates the physical and behavioral abnormalities displayed by the transgenic, nonhuman mammal as a result of overactivity of a mammalian LPA receptor, the alleviation of the abnormality identifying the compound as an antagonist. This invention also provides an antagonist identified by this method. This invention also provides for a pharmaceutical composition comprising an antagonist identified by this method and a pharmaceutically acceptable carrier.

This invention further provides for a method of treating an abnormality in a subject wherein the abnormality is alleviated by decreasing the activity of a mammalian LPA receptor which comprises administering to the subject an effective amount of this pharmaceutical composition, thereby treating the abnormality.

This invention provides for a method for identifying an agonist capable of alleviating an abnormality in a subject wherein the abnormality is alleviated by increasing the activity of a mammalian LPA receptor comprising administering a compound to the transgenic, nonhuman mammal, and determining whether the compound alleviates the physical and behavioral abnormalities displayed by the transgenic, nonhuman mammal, the alleviation of the abnormality identifying the compound as an agonist. This invention also provides for an agonist identified by this method. This invention also provides for a pharmaceutical composition comprising an agonist identified by this method and a pharmaceutically acceptable carrier. This invention further provides for a method of treating an abnormality in a subject wherein the abnormality is alleviated by increasing the activity of a mammalian LPA receptor which comprises administering to the subject an effective amount of this pharmaceutical composition, thereby treating the abnormality.

This invention provides for a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian LPA receptor and labeled with a detectable marker; (e) detecting labeled bands which have hybridized to the DNA encoding a mammalian LPA receptor labeled with a detectable marker to create a unique band pattern specific to the DNA of subjects suffering from the disorder; (f) preparing DNA obtained for diagnosis by steps (a)–(e); and (g) comparing the unique band pattern specific to the DNA of subjects suffering from the disorder from step (e) and the DNA obtained for diagnosis from step (f) to determine whether the patterns are the same or different and to diagnose thereby predisposition to the disorder if the patterns are the same.

This invention provides for a method of preparing the purified mammalian LPA receptor which comprises: (a) inducing cells to express the mammalian LPA receptor; (b) recovering the mammalian LPA receptor from the induced cells; and (c) purifying the mammalian LPA receptor so recovered.

This invention provides a method of preparing the purified mammalian LPA receptor which comprises: (a) inserting nucleic acid encoding the mammalian LPA receptor in a suitable vector; (b) introducing the resulting vector in a suitable host cell; (c) placing the resulting cell in suitable condition permitting the production of the isolated mammalian LPA receptor; (d) recovering the mammalian LPA receptor produced by the resulting cell; and (e) purifying the mammalian LPA receptor so recovered.

This invention provides for process for determining whether a chemical compound is an mammalian LPA receptor agonist which comprises contacting cells transfected with and expressing DNA encoding the mammalian LPA receptor with the compound under conditions permitting the activation of the mammalian LPA receptor, and detecting an increase in mammalian LPA receptor activity, so as to thereby determine whether the compound is a mammalian LPA receptor agonist. This invention further provides for a pharmaceutical composition which comprises an amount of mammalian LPA receptor agonist determined by the above-described process effective to increase activity of a mammalian LPA receptor and a pharmaceutically acceptable carrier.

This invention provides for a process for determining whether a chemical compound is a mammalian LPA receptor antagonist which comprises contacting cells transfected with and expressing DNA encoding the mammalian LPA receptor with the compound in the presence of a known mammalian LPA receptor agonist, under conditions permitting the activation of the mammalian LPA receptor, and detecting a decrease in mammalian LPA receptor activity, so as to thereby determine whether the compound is a mammalian LPA receptor antagonist.

This invention further provides for a pharmaceutical composition which comprises an amount of mammalian LPA receptor antagonist determined by the above-described process effective to reduce activity of a mammalian LPA receptor and a pharmaceutically acceptable carrier.

This invention provides for a process for determining whether a chemical compound specifically binds to and activates a mammalian LPA receptor, which comprises contacting cells producing a second messenger response and expressing on their cell surface the mammalian LPA receptor, wherein such cells do not normally express the mammalian LPA receptor, with the chemical compound under conditions suitable for activation of the mammalian LPA receptor, and measuring the second messenger response in the presence and in the absence of the chemical compound, a change in the second messenger response in the presence of the chemical compound indicating that the compound activates the mammalian LPA receptor. This invention further provides for a pharmaceutical composition which comprises an amount of mammalian LPA receptor agonist determined by the above-described process effective to increase activity of a mammalian LPA receptor and a pharmaceutically acceptable carrier.

This invention provides for a process for determining whether a chemical compound specifically binds to and inhibits activation of a mammalian LPA receptor, which comprises separately contacting cells producing a second messenger response and expressing on their cell surface the mammalian LPA receptor, wherein such cells do not normally express the mammalian LPA receptor, with both the chemical compound and a second chemical compound known to activate the mammalian LPA receptor, and with only the second chemical compound, under conditions suitable for activation of the mammalian LPA receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the mammalian LPA receptor. This invention further provides for a pharmaceutical composition which comprises an amount of mammalian LPA receptor antagonist determined by the above-described process effective to reduce activity of a mammalian LPA receptor and a pharmaceutically acceptable carrier.

This invention provides for a method of screening a plurality of chemical compounds not known to activate a mammalian LPA receptor to identify a compound which activates the mammalian LPA receptor which comprises: (a) contacting cells transfected with and expressing the mammalian LPA receptor with the plurality of compounds not known to activate the mammalian LPA receptor, under conditions permitting activation of the mammalian LPA receptor; (b) determining whether the activity of the mammalian LPA receptor is increased in the presence of the compounds; and if so (c) separately determining whether the activation of the mammalian LPA receptor is increased by each compound included in the plurality of compounds, so as to thereby identify the compound which activates the mammalian LPA receptor. This invention further provides for a pharmaceutical composition which comprises an amount of mammalian LPA receptor agonist determined by the above-described process effective to increase activity of a mammalian LPA receptor and a pharmaceutically acceptable carrier.

This invention provides for a method of screening a plurality of chemical compounds not known to inhibit the activation of a mammalian LPA receptor to identify a compound which inhibits the activation of the mammalian LPA receptor, which comprises: (a) contacting cells transfected with and expressing the mammalian LPA receptor with the plurality of compounds in the presence of a known mammalian LPA receptor agonist, under conditions permitting activation of the mammalian LPA receptor; (b) determining whether the activation of the mammalian LPA receptor is reduced in the presence of the plurality of compounds, relative to the activation of the mammalian LPA receptor in the absence of the plurality of compounds; and if so (c) separately determining the inhibition of activation of the mammalian LPA receptor for each compound included in the plurality of compounds, so as to thereby identify the compound which inhibits the activation of the mammalian LPA receptor. This invention further provides for a pharmaceutical composition which comprises an amount of mammalian LPA receptor antagonist determined by the above-described process effective to decrease activity of a mammalian LPA receptor and a pharmaceutically acceptable carrier.

This invention provides for a method of treating an abnormality in a subject wherein the abnormality is alleviated by increasing the activity of a mammalian LPA receptor which comprises administering to the subject an amount of compound which is a mammalian LPA receptor agonist effective to treat the abnormality.

This invention provides for a method of treating an abnormality in a subject wherein the abnormality is alleviated by decreasing the activity of a mammalian LPA receptor which comprises administering to the subject an amount of compound which is a mammalian LPA receptor antagonist effective to treat the abnormality.

BRIEF DESCRIPTION OF THE FIGURES

FIGS. 1A–1C

Nucleotide sequences encoding two human LPA receptors are shown. The smaller of these sequences is included within the larger. In addition, partial 5' and 3' untranslated sequences are shown. This entire sequence is designated as Seq. I.D. No. 1. In FIGS. 1A–1C, two start (ATG) codons (at positions 167–169 and 350–352) and one stop (TAG) codon (at position 1466–1468) are underlined. Using the downstream ATG (at position 350–352), with a better Kozak consensus site (Kozak, 1991), results in an open reading frame of 1116 nucleotides. The upstream ATG (at position 167–169) results in a reading frame containing 1299 nucleotides.

FIGS. 2A–2B

Nucleotide sequence (Seq. I.D. No. 2) encoding a human LPA receptor. The coding sequence starts from the start codon at positions 350–352 of the smaller reading frame shown in FIGS. 1A–1C and ends at the termination codon at positions 1466–1468 shown in FIGS. 1A–1C.

FIGS. 3A–3B

Deduced amino acid sequence (Seq. I.D. No. 3) of the human LPA receptor encoded by the nucleotide sequence shown in FIG. 2A–2B (Seq. I.D. No. 2). Seven solid lines designated I-VII located above portions of the sequence indicate the seven putative transmembrane (TM) spanning regions.

FIGS. 4A–4D

Sequence alignment comprising the nucleotide coding sequence (Seq. I.D. No. 2) of the human LPA receptor and the corresponding nucleotide coding sequence of the Xenopus LPA receptor (Seq. I.D. No. 4) (Guo, 1996). The nucleotide coding sequence of the human LPA receptor (first top line) is aligned with the corresponding nucleotide coding sequence of the Xenopus LPA receptor.

DETAILED DESCRIPTION OF THE INVENTION

Throughout this application, the following standard abbreviations are used to indicate specific nucleotide bases:

A=adenine
G=guanine
C=cytosine
T=thymine
U=uracil
M=adenine or cytosine
R=adenine or guanine
W=adenine, thymine, or uracil
S=cytosine or guanine
Y=cytosine, thymine, or uracil
K=guanine, thymine, or uracil
V=adenine, cytosine, guanine (not thymine or uracil)
H=adenine, cytosine, thymine, or uracil (not guanine)
D=adenine, guanine, thymine, or uracil (not cytosine)
B=cytosine, guanine, thymine, or uracil (not adenine)
N=adenine, cytosine, guanine, thymine, or uracil (or other modified base such as inosine)
i=inosine Furthermore, the term "agonist" is used throughout this application to indicate any peptide or non-peptidyl compound which increases the activity of any of the polypeptides of the subject invention. The term "antagonist" is used throughout this application to indicate any peptide or non-peptidyl compound which decreases the activity of any of the polypeptides of the subject invention.

The activity of a G-protein coupled receptor such as the polypeptides disclosed herein may be measured using any of a variety of functional assays in which activation of the receptor in question results in an observable change in the level of some second messenger system, including but not limited to adenylate cyclase, calcium mobilization, arachidonic acid release, ion channel activity, inositol phospholipid hydrolysis or guanylyl cyclase. Heterologous expression systems utilizing appropriate host cells to express the nucleic acid of the subject invention are used to obtain the desired second messenger coupling. Receptor activity may also be assayed in an occyte expression system.

It is possible that the mammalian LPA receptor contains introns and furthermore, the possibility exists that additional introns could exist in coding or non-coding regions. In addition, spliced form(s) of mRNA may encode additional amino acids either upstream of the currently defined starting methionine or within the coding region. Further, the existence and use of alternative exons is possible, whereby the mRNA may encode different amino acids within the region comprising the exon. In addition, single amino acid substitutions may arise via the mechanism of RNA editing such that the amino acid sequence of the expressed protein is different than that encoded by the original gene (Burns et al., 1996; Chu et al., 1996). Such variants may exhibit pharmacologic properties differing from the polypeptide encoded by the original gene.

This invention provides a splice variant of the mammalian LPA receptor disclosed herein. This invention further provides for alternate translation initiation sites and alternately spliced or edited variants of nucleic acids encoding mammalian LPA receptors of this invention.

This invention provides the above-described isolated nucleic acid, wherein the nucleic acid is DNA. In an embodiment, the DNA is cDNA. In another embodiment, the DNA is genomic DNA. In still another embodiment, the nucleic acid molecule is RNA. Methods for production and manipulation of nucleic acid molecules are well known in the art.

This invention further provides nucleic acid which is degenerate with respect to the DNA comprising the coding sequence of the plasmid HL-18a.

This invention also encompasses DNAs and cDNAs which encode amino acid sequences which differ from those of the polypeptides of this invention, but which should not produce phenotypic changes. Alternatively, this invention also encompasses DNAs, cDNAs, and RNAs which hybridize to the DNA, cDNA, and RNA of the subject invention. Hybridization methods are well known to those of skill in the art.

The nucleic acids of the subject invention also include nucleic acid molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The modified polypeptides of this invention may be transfected into cells either transiently or stably using methods well-known in the art, examples of which are disclosed herein. This invention also provides for binding assays using the modified polypeptides, in which the polypeptide is expressed either transiently or in stable cell lines. This invention further provides for a compound identified using a modified polypeptide in a binding assay such as the binding assays described herein.

The nucleic acids described and claimed herein are useful for the information which they provide concerning the amino acid sequence of the polypeptide and as products for the large scale synthesis of the polypeptide by a variety of recombinant techniques. The nucleic acid molecule is useful for generating new cloning and expression vectors, transformed and transfected prokaryotic and eukaryotic host cells, and new and useful methods for cultured growth of such host cells capable of expression of the polypeptide and related products.

This invention provides for an isolated nucleic acid encoding a mammalian LPA receptor. In one embodiment, the nucleic acid is DNA. In another embodiment, the DNA in cDNA. In another embodiment, the DNA is genomic DNA. In another embodiment, the nucleic acid is RNA.

In an embodiment of the present invention, the mammalian LPA receptor is a human LPA receptor. In an embodiment, the nucleic acid encodes a mammalian LPA receptor which has substantially the same amino acid sequence as does the mammalian LPA receptor encoded by the plasmid HL-18a (ATCC Accession No. 209448). In another embodiment, the nucleic acid encodes a human LPA receptor which has an amino acid sequence identical to that encoded by the plasmid HL-18a (ATCC Accession No. 209448). In another embodiment, the human LPA receptor has an amino acid sequence, substantially the same as the amino acid sequence shown in FIG. 3 (Seq. I.D. No. 3). In another embodiment, the human LPA receptor has an amino acid sequence identical to the amino acid sequence shown in FIG. 3 (Seq. I.D. No. 3).

This invention provides an isolated nucleic acid encoding a modified mammalian LPA receptor, which differs from a mammalian LPA receptor by having an amino acid(s) deletion, replacement, or addition in the third intracellular domain.

This invention provides for a purified mammalian LPA receptor protein.

This invention provides a vector comprising the nucleic acid of a mammalian LPA receptor. In a further embodiment, the mammalian LPA receptor is a human LPA receptor.

In an embodiment, the vector is adapted for expression in a bacterial cell which comprises the regulatory elements necessary for expression of the nucleic acid in the bacterial cell operatively linked to the nucleic acid encoding a mammalian LPA receptor as to permit expression thereof. In another embodiment, the vector is adapted for expression in an amphibian cell which comprises the regulatory elements necessary for expression of the nucleic acid in the amphibian cell operatively linked to the nucleic acid encoding a mammalian LPA receptor as to permit expression thereof. In another embodiment, the vector is adapted for expression in a yeast cell which comprises the regulatory elements necessary for expression of the nucleic acid in the yeast cell operatively linked to the nucleic acid encoding a mammalian LPA receptor so as to permit expression thereof. In another embodiment, the vector is adapted for expression in an insect cell which comprises the regulatory elements necessary for expression of the nucleic acid in the insect cell operatively linked to the nucleic acid encoding a mammalian LPA receptor so as to permit expression thereof. In another embodiment, the vector is a baculovirus. In another embodiment, the vector is adapted for expression in a mammalian cell which comprises the regulatory elements necessary for expression of the nucleic acid in the mammalian cell operatively linked to the nucleic acid encoding a mammalian LPA receptor so as to permit expression thereof. In a further embodiment, the vector is a plasmid.

This invention provides a plasmid designated HL-18a (ATCC Accession No. 209448). This plasmid comprises the regulatory elements necessary for expression of DNA in a mammalian cell operatively linked to DNA encoding the mammalian LPA receptor so as to permit expression thereof.

This plasmid (HL-18a) was deposited on Nov. 11, 1997, with the American Type Culture Collection (ATCC), 10801 University Boulevard, Manassas, Va. 20110-2209 under the provisions of the Budapest Treaty for the International Recognition of the Deposit of Microorganisms for the Purposes of Patent Procedure and was accorded ATCC Accession No. 209448.

This invention further provides for any vector or plasmid which comprises modified untranslated sequences, which are beneficial for expression in desired host cells or for use in binding or functional assays. For example, a vector or plasmid with untranslated sequences of varying lengths may express differing amounts of the polypeptide depending upon the host cell used. In an embodiment, the vector or plasmid comprises the coding sequence of the polypeptide and the regulatory elements necessary for expression in the host cell.

This invention provides a cell comprising the vector comprising a nucleic acid encoding the mammalian LPA receptor. In an embodiment, the cell is a non-mammalian cell. In another embodiment, the non-mammalian cell is a Xenopus oocyte cell or a Xenopus melanophore cell. In another embodiment, the cell is a mammalian cell. In a further embodiment, the mammalian cell is a COS-7 cell, a 293 human embryonic kidney cell, a NIH-3T3 cell, a LM(tk–) cell, a mouse Y1 cell, or a CHO cell.

This invention provides for an insect cell comprising a vector adapted for expression in an insect cell comprising a nucleic acid encoding a mammalian LPA receptor. In a further embodiment, the insect cell is an Sf9 cell, an Sf21 cell or a HighFive cell.

This invention provides for a membrane preparation isolated from any of the cells described above.

This invention provides a nucleic acid probe comprising at least 15 nucleotides, which probe specifically hybridizes with a nucleic acid encoding a mammalian LPA receptor, wherein the probe has a unique sequence corresponding to a sequence present within one of the two strands of the nucleic acid which encode the mammalian LPA receptor contained in plasmid HL-18a. This invention also provides a nucleic acid probe comprising at least 15 nucleotides, which probe specifically hybridizes with a nucleic acid encoding a mammalian LPA receptor, wherein the probe has a unique sequence corresponding to a sequence present within (a) the nucleic acid sequence shown in FIG. 2 (Seq. I.D. No. 2) or (b) the reverse complement thereto. In an embodiment, the nucleic acid is DNA. In another embodiment, the nucleic acid is RNA.

This invention provides for a nucleic acid probe comprising a nucleic acid molecule of at least 15 nucleotides which is complementary to a unique fragment of the sequence of a nucleic acid molecule encoding a mammalian LPA receptor. This invention also provides for a nucleic acid probe comprising a nucleic acid molecule of at least 15 nucleotides which is complementary to the antisense sequence of a unique fragment of the sequence of a nucleic acid molecule encoding a mammalian LPA receptor.

As used herein, the phrase "specifically hybridizing" means the ability of a nucleic acid molecule to recognize a nucleic acid sequence complementary to its own and to form double-helical segments through hydrogen bonding between complementary base pairs.

Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes the polypeptides of this invention into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the DNA molecule which encodes the polypeptides of this invention downstream of a bacteriophage promoter such as T3, T7 or SP6. Large amounts of RNA probe may be produced by incubating the labeled nucleotides with the linearized fragment where it contains an upstream promoter in the presence of the appropriate RNA polymerase.

This invention provides for an antisense oligonucleotide having a sequence capable of specifically hybridizing to the RNA encoding a mammalian LPA receptor, so as to prevent translation of the RNA. This invention also provides for an antisense oligonucleotide having a sequence capable of specifically hybridizing to the genomic DNA encoding a mammalian LPA receptor. In an embodiment, the antisense oligonucleotide comprises chemically modified nucleotides or nucleotide analogues.

This invention provides an antibody capable of binding to a mammalian LPA receptor. In an embodiment, the mammalian LPA receptor is a human LPA receptor. This invention also provides a agent capable of competitively inhibiting the binding of the antibody to a mammalian LPA receptor. In a further embodiment, the antibody is a monoclonal antibody or antisera.

This invention provides for a pharmaceutical composition comprising (a) an amount of an oligonucleotide capable of passing through a cell membrane and effective to reduce expression of a mammalian LPA receptor and (b) a pharmaceutically acceptable carrier capable of passing through a cell membrane. In an embodiment, the oligonucleotide is coupled to a substance which inactivates mRNA. In a further embodiment, the substance which inactivates mRNA is a ribozyme. In another embodiment, the pharmaceutically acceptable carrier comprises a structure which binds to a mammalian LPA receptor on a cell capable of being taken up by the cells after binding to the structure. In a further embodiment, the pharmaceutically acceptable carrier is capable of binding to a mammalian LPA receptor which is specific for a selected cell type.

This invention provides a pharmaceutical composition which comprises an amount of the antibody effective to block binding of a ligand to a human LPA receptor and a pharmaceutically acceptable carrier.

As used herein, "pharmaceutically acceptable carriers" means any of the standard pharmaceutically acceptable carriers. Examples include, but are not limited to, phosphate buffered saline, physiological saline, water and emulsions, such as oil/water emulsions.

This invention provides for a transgenic, nonhuman mammal expressing the DNA encoding a mammalian LPA receptor. This invention also provides for a transgenic, nonhuman mammal comprising a homologous recombination knockout of the native mammalian LPA receptor. This invention further provides for a transgenic, nonhuman mammal whose genome comprises antisense DNA complementary to the DNA encoding a mammalian LPA receptor so placed within the genome as to be transcribed into antisense mRNA which is complementary to mRNA encoding a mammalian LPA receptor and which hybridizes to mRNA encoding a mammalian LPA receptor, thereby reducing its translation. In an embodiment, the DNA encoding a mammalian LPA receptor additionally comprises an inducible promoter. In a further embodiment, the DNA encoding a mammalian LPA receptor additionally comprises tissue specific regulatory elements. In another embodiment, the transgenic, nonhuman mammal is a mouse.

Animal model systems which elucidate the physiological and behavioral roles of the polypeptides of this invention are produced by creating transgenic animals in which the activity of the polypeptide is either increased or decreased, or the amino acid sequence of the expressed polypeptide is altered, by a variety of techniques. Examples of these techniques include, but are not limited to: 1) Insertion of normal or mutant versions of DNA encoding the polypeptide, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus in transgenic animals to alter the regulation of expression or the structure of these polypeptide sequences. The technique of homologous recombination is well known in the art. It replaces the native gene with the inserted gene and so is useful for producing an animal that cannot express native polypeptides but does express, for example, an inserted mutant polypeptide, which has replaced the native polypeptide in the animal's genome by recombination, resulting in underexpression of the transporter. Microinjection adds genes to the genome, but does not remove them, and so is useful for producing an animal which expresses its own and added polypeptides, resulting in overexpression of the polypeptides.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a polypeptide of this invention is purified from a vector by methods well known in the art. Inducible promoters may be fused with the coding region of the DNA to provide an experimental means to regulate expression of the trans-gene. Alternatively, or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

This invention provides for a process for identifying a chemical compound which specifically binds to a mammalian LPA receptor which comprises contacting cells containing DNA encoding and expressing on their cell surface the mammalian LPA receptor, wherein such cells do not normally express the mammalian LPA receptor, with the compound under conditions suitable for binding, and detecting specific binding of the chemical compound to the mammalian LPA receptor. This invention also provides a process for identifying a chemical compound which specifically binds to a mammalian LPA receptor which comprises contacting a membrane fragment from a cell extract of cells containing DNA encoding and expressing on their cell surface the mammalian LPA receptor, wherein such cells do not normally express the mammalian LPA receptor, with the compound under conditions suitable for binding, and detecting specific binding of the chemical compound to the mammalian LPA receptor. In an embodiment, the mammalian LPA receptor is a human LPA receptor. In a further embodiment, the mammalian LPA receptor has substantially the same amino acid sequence as encoded by plasmid HL-18a (ATCC Accession No. 209448). In a further embodiment, the mammalian LPA receptor has substantially the same amino acid sequence as shown in FIG. 3 (Seq. I.D. No. 3). In another embodiment, the mammalian LPA receptor has the amino acid sequence shown in FIG. 3 (Seq. I.D. No. 3). In another embodiment, the compound is a compound not previously known to bind to a mammalian LPA receptor. This invention further provides a compound determined by the above-described process.

In a further embodiment the cell is an insect cell. In another embodiment, the cell is a mammalian cell. In another embodiment, the cell is non-neuronal in origin. In a further embodiment, the non-neuronal cell is a COS-7 cell, 293 human embryonic kidney cell, a CHO cell, a NIH-3T3 cell, a mouse Y1 cell, or a LM(tk-) cell. In another embodiment, the compound is a compound not previously known to bind to a mammalian LPA receptor. In a further embodiment, the compound is determined by the above-described process.

This invention provides process involving competitive binding for identifying a chemical compound which specifically binds to a mammalian LPA receptor which comprises separately contacting cells expressing on their cell surface the mammalian LPA receptor, wherein such cells do not normally express the mammalian LPA receptor, with both the chemical compound and a second chemical compound known to bind to the receptor, and with only the second chemical compound, under conditions suitable for binding of both compounds, and detecting specific binding of the chemical compound to the mammalian LPA receptor, a decrease in the binding of the second chemical compound to the mammalian LPA receptor in the presence of the chemical compound indicating that the chemical compound binds to the mammalian LPA receptor.

This invention also provides a process involving competitive binding for identifying a chemical compound which specifically binds to a mammalian LPA receptor which comprises separately contacting a membrane fraction from a cell extract of cells expressing on their cell surface the mammalian LPA receptor, wherein such cells do not normally express the mammalian LPA receptor, with both the chemical compound and a second chemical compound known to bind to the receptor, and with only the second chemical compound, under conditions suitable for binding of both compounds, and detecting specific binding of the chemical compound to the mammalian LPA receptor, a decrease in the binding of the second chemical compound to the mammalian LPA receptor in the presence of the chemical compound indicating that the chemical compound binds to the mammalian LPA receptor.

In an embodiment, the mammalian LPA receptor is a human LPA receptor. In another embodiment, the human LPA receptor has substantially the same amino acid sequence as encoded by plasmid HL-18a (ATCC Accession No. 209448). In another embodiment, the mammalian LPA receptor has substantially the same amino acid sequence as shown in FIG. 3 (Seq. I.D. No. 3). In another embodiment, the mammalian LPA receptor has the amino acid sequence shown in FIG. 3 (Seq. I.D. No. 3).

In another embodiment, the cell is an insect cell. In another embodiment, the cell is a mammalian cell. In another embodiment, the cell is non-neuronal in origin. In a further embodiment, the non-neuronal cell is a COS-7 cell, 293 human embryonic kidney cell, a CHO cell, a NIH-3T3 cell, a mouse Y1 cell, or a LM(tk-) cell. In another embodiment, the compound is a compound not previously known to bind to a mammalian LPA receptor. This invention also provides for a compound determined by the above-described process.

This invention provides a method of screening a plurality of chemical compounds not known to bind to a mammalian LPA receptor to identify a compound which specifically binds to the mammalian LPA receptor, which comprises (a) contacting cells transfected with and expressing DNA encoding the mammalian LPA receptor with a compound known to bind specifically to the mammalian LPA receptor; (b) contacting the preparation of step (a) with the plurality of compounds not known to bind specifically to the mammalian LPA receptor, under conditions permitting binding of compounds known to bind the mammalian LPA receptor; (c) determining whether the binding of the compound known to bind to the mammalian LPA receptor is reduced in the presence of the compounds within the plurality of compounds, relative to the binding of the compound in the absence of the plurality of compounds; and if so (d) separately determining the binding to the mammalian LPA receptor of compounds included in the plurality of compounds, so as to thereby identify the compound which specifically binds to the mammalian LPA receptor.

This invention provides for a method of screening a plurality of chemical compounds not known to bind to a mammalian LPA receptor to identify a compound which specifically binds to the mammalian LPA receptor, which comprises (a) preparing a cell extract from cells transfected with and expressing DNA encoding the mammalian LPA receptor, isolating a membrane fraction from the cell extract, contacting the membrane fraction with a compound known to bind specifically to the mammalian LPA receptor; (b) contacting the preparation of step (a) with the plurality of compounds not known to bind specifically to the mammalian LPA receptor, under conditions permitting binding of compounds known to bind the mammalian LPA receptor; (c) determining whether the binding of the compound known to bind to the mammalian LPA receptor is reduced in the presence of the compounds within the plurality of compounds, relative to the binding of the compound in the absence of the plurality of compounds; and if so (d) separately determining the binding to the mammalian LPA receptor of compounds included in the plurality of compounds, so as to thereby identify the compound which specifically binds to the mammalian LPA receptor.

In an embodiment, the mammalian LPA receptor is a human LPA receptor. In another embodiment, the cell is a mammalian cell. In another embodiment, the mammalian cell is non-neuronal in origin. In a further embodiment, the non-neuronal cell is a COS-7 cell, a 293 human embryonic kidney cell, a LM(tk–) cell, a CHO cell, a mouse Y1 cell, or an NIH-3T3 cell.

This invention provides a method of detecting expression of a mammalian LPA receptor by detecting the presence of mRNA coding for the mammalian LPA receptor which comprises obtaining total mRNA from the cell and contacting the mRNA so obtained from the nucleic acid probe under hybridizing conditions, detecting the presence of mRNA hybridizing to the probe, and thereby detecting the expression of the mammalian LPA receptor by the cell.

This invention provides for a method of detecting the presence of a mammalian LPA receptor on the surface of a cell which comprises contacting the cell with the antibody under conditions permitting binding of the antibody to the receptor, detecting the presence of the antibody bound to the cell, and thereby detecting the presence of a mammalian LPA receptor on the surface of the cell.

This invention provides a method of determining the physiological effects of varying levels of activity of mammalian LPA receptors which comprises producing a transgenic, nonhuman mammal whose levels of mammalian LPA receptor activity are varied by use of an inducible promoter which regulates mammalian LPA receptor expression.

This invention provides a method of determining the physiological effects of varying levels of activity of mammalian LPA receptors which comprises producing a panel of transgenic, nonhuman mammals each expressing a different amount of mammalian LPA receptor.

This invention provides a method for identifying an antagonist capable of alleviating an abnormality wherein the abnormality is alleviated by decreasing the activity of a mammalian LPA receptor comprising administering a compound to the transgenic, nonhuman mammal and determining whether the compound alleviates the physical and behavioral abnormalities displayed by the transgenic, nonhuman mammal as a result of overactivity of a mammalian LPA receptor, the alleviation of the abnormality identifying the compound as an antagonist. This invention provides an antagonist identified by the above-described method. This invention further provides a pharmaceutical composition comprising an antagonist identified by the above-described method and a pharmaceutically acceptable carrier. This invention further provides a method of treating an abnormality in a subject wherein the abnormality is alleviated by decreasing the activity of a mammalian LPA receptor which comprises administering to the subject an effective amount of the pharmaceutical composition, thereby treating the abnormality.

This invention provides a method for identifying an agonist capable of alleviating an abnormality in a subject wherein the abnormality is alleviated by increasing the activity of a mammalian LPA receptor comprising administering a compound to the transgenic, nonhuman mammal, and determining whether the compound alleviates the physical and behavioral abnormalities displayed by the transgenic, nonhuman mammal, the alleviation of the abnormality identifying the compound as an agonist. This invention also provides an agonist identified by the above-described method. This invention further provides a pharmaceutical composition comprising an agonist identified by the above-described method and a pharmaceutically acceptable carrier. This invention further provides a method of treating an abnormality in a subject wherein the abnormality is alleviated by increasing the activity of a mammalian LPA receptor which comprises administering to the subject an effective amount of the pharmaceutical composition, thereby treating the abnormality.

This invention provides for a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian LPA receptor and labeled with a detectable marker; (e) detecting labeled bands which have hybridized to the DNA encoding a mammalian LPA receptor labeled with a detectable marker to create a unique band pattern specific to the DNA of subjects suffering from the disorder; (f) preparing DNA obtained for diagnosis by steps (a)–(e); and (g) comparing the unique band pattern specific to the DNA of subjects suffering from the disorder from step (e) and the DNA obtained for diagnosis from step (f) to determine whether the patterns are the same or different and to diagnose thereby predisposition to the disorder if the patterns are the same. In an embodiment, the disorder associated with the activity of a specific mammalian allele is diagnosed.

This invention provides a method of preparing the purified mammalian LPA receptor which comprises: (a) inducing cells to express the mammalian LPA receptor; (b) recovering the mammalian LPA receptor from the induced cells; and (c) purifying the mammalian LPA receptor so recovered.

This invention provides a method of preparing the purified mammalian LPA receptor which comprises: (a) inserting nucleic acid encoding the mammalian LPA receptor in a suitable vector; (b) introducing the resulting vector in a suitable host cell; (c) placing the resulting cell in suitable condition permitting the production of the isolated mammalian LPA receptor; (d) recovering the mammalian LPA receptor produced by the resulting cell; and (e) purifying the mammalian LPA receptor so recovered.

This invention provides a process for determining whether a chemical compound is an mammalian LPA receptor agonist which comprises contacting cells transfected with and expressing DNA encoding the mammalian LPA receptor with the compound under conditions permitting the activation of the mammalian LPA receptor, and detecting an increase in mammalian LPA receptor activity, so as to thereby determine whether the compound is a mammalian LPA receptor agonist. This invention also provides a process for determining whether a chemical compound is a mammalian LPA receptor antagonist which comprises contacting cells transfected with and expressing DNA encoding the mammalian LPA receptor with the compound in the presence of a known mammalian LPA receptor agonist, under conditions permitting the activation of the mammalian LPA receptor, and detecting a decrease in mammalian LPA receptor activity, so as to thereby determine whether the compound is a mammalian LPA receptor antagonist. In an embodiment, the mammalian LPA receptor is a human LPA receptor.

This invention provides a pharmaceutical composition which comprises an amount of a mammalian LPA receptor agonist determined by the above-described process effective to increase activity of a mammalian LPA receptor and a pharmaceutically acceptable carrier. In a further embodiment, the mammalian LPA receptor agonist is not previously known.

This invention provides for a pharmaceutical composition which comprises an amount of a mammalian LPA receptor antagonist determined by the above-described process effective to reduce activity of a mammalian LPA receptor and a pharmaceutically acceptable carrier. In a further embodiment, the mammalian LPA receptor antagonist is not previously known.

This invention provides a process for determining whether a chemical compound specifically binds to and activates a mammalian LPA receptor, which comprises contacting cells producing a second messenger response and expressing on their cell surface the mammalian LPA receptor, wherein such cells do not normally express the mammalian LPA receptor, with the chemical compound under conditions suitable for activation of the mammalian LPA receptor, and measuring the second messenger response in the presence and in the absence of the chemical compound, a change in the second messenger response in the presence of the chemical compound indicating that the compound activates the mammalian LPA receptor. In an embodiment, the second messenger response comprises chloride channel activation and the change in second messenger is an increase in the level of inward chloride current.

This invention provides a process for determining whether a chemical compound specifically binds to and inhibits activation of a mammalian LPA receptor, which comprises separately contacting cells producing a second messenger response and expressing on their cell surface the mammalian LPA receptor, wherein such cells do not normally express the mammalian LPA receptor, with both the chemical compound and a second chemical compound known to activate the mammalian LPA receptor, and with only the second chemical compound, under conditions suitable for activation of the mammalian LPA receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the mammalian LPA receptor. In a further embodiment, the second messenger response comprises chloride channel activation and the change in second messenger response is a smaller increase in the level of inward chloride current in the presence of both the chemical compound and the second chemical compound than in the presence of only the second chemical compound.

In an embodiment, the mammalian LPA receptor is a human LPA receptor. In another embodiment, the human LPA receptor has substantially the same amino acid sequence as encoded by the plasmid HL-18a (ATCC Accession No. 209448). In another embodiment, the human LPA receptor has substantially the same amino acid sequence as that shown in FIG. 3 (Seq. I.D. No. 3). In another embodiment, the human LPA receptor has an amino acid sequence, identical to the amino acid sequence shown in FIG. 3 (Seq. I.D. No. 3).

In another embodiment, the cell is an insect cell. In another embodiment, the cell is a mammalian cell. In another embodiment, the mammalian cell is non-neuronal in origin. In a further embodiment, the non-neuronal cell is a COS-7 cell, CHO cell, 293 human embryonic kidney cell, NIH-3T3 cell or LM(tk−) cell. In another embodiment, the compound is not previously known to bind to a mammalian LPA receptor. In another embodiment, the compound is determined by the above-described process.

This invention provides for a pharmaceutical composition which comprises an amount of a mammalian LPA receptor agonist determined by the above-described process effective to increase activity of a mammalian LPA receptor and a pharmaceutically acceptable carrier.

In a further embodiment, the mammalian LPA receptor agonist is not previously known.

This invention provides for a pharmaceutical composition which comprises an amount of a mammalian LPA receptor antagonist determined by the above-described process effective to reduce activity of a mammalian LPA receptor and a pharmaceutically acceptable carrier. In a further embodiment, the mammalian LPA receptor antagonist is not previously known.

This invention provides a method of screening a plurality of chemical compounds not known to activate a mammalian LPA receptor to identify a compound which activates the mammalian LPA receptor which comprises: (a) contacting cells transfected with and expressing the mammalian LPA receptor with the plurality of compounds not known to activate the mammalian LPA receptor, under conditions permitting activation of the mammalian LPA receptor; (b) determining whether the activity of the mammalian LPA receptor is increased in the presence of the compounds; and if so (c) separately determining whether the activation of the mammalian LPA receptor is increased by each compound included in the plurality of compounds, so as to thereby identify the compound which activates the mammalian LPA receptor. In a further embodiment, the mammalian LPA receptor is a human LPA receptor.

This invention provides a method of screening a plurality of chemical compounds not known to inhibit the activation of a mammalian LPA receptor to identify a compound which inhibits the activation of the mammalian LPA receptor, which comprises: (a) contacting cells transfected with and expressing the mammalian LPA receptor with the plurality of compounds in the presence of a known mammalian LPA receptor agonist, under conditions permitting activation of the mammalian LPA receptor; (b) determining whether the activation of the mammalian LPA receptor is reduced in the presence of the plurality of compounds, relative to the activation of the mammalian LPA receptor in the absence of the plurality of compounds; and if so (c) separately determining the inhibition of activation of the mammalian LPA receptor for each compound included in the plurality of compounds, so as to thereby identify the compound which inhibits the activation of the mammalian LPA receptor. In an embodiment, the mammalian LPA receptor is a human LPA receptor.

In another embodiment, the cell is a mammalian cell. In another embodiment, the mammalian cell is non-neuronal in origin. In another embodiment, the non-neuronal cell is a COS-7 cell, a 293 human embryonic kidney cell, a LM(tk–) cell or an NIH-3T3 cell.

This invention also provides a pharmaceutical composition comprising a compound identified by the above-described method effective to increase mammalian LPA receptor activity and a pharmaceutically acceptable carrier.

This invention also provides a pharmaceutical composition comprising a compound identified by the above-described methods effective to decrease mammalian LPA receptor activity and a pharmaceutically acceptable carrier.

This invention further provides a method of measuring polypeptide activation in an oocyte expression system such as a Xenopus oocyte or melanophore. In an embodiment, polypeptide activation is determined by measurement of ion channel activity. In another embodiment, polypeptide activation is measured by aequorin luminescence.

Expression of genes in Xenopus oocytes is well known in the art (Coleman,A., 1984; Masu, Y. et al., 1994) and is performed using microinjection of native mRNA or in vitro synthesized mRNA into frog oocytes. The preparation of in vitro synthesized mPNA can be performed by various standard techniques (Sambrook et al.,1989) including using T7 polymerase with the mCAP RNA capping kit (Stratagene).

This invention provides a method of treating an abnormality in a subject wherein the abnormality is alleviated by increasing the activity of a mammalian LPA receptor which comprises administering to the subject an amount of compound which is a mammalian LPA receptor agonist effective to treat the abnormality.

In an embodiment, the abnormality is a wound or tissue or cosmetic defect in which the agonist would activate wound healing, tissue regeneration (preferably skin or nerve regeneration), or cosmetic augmentation. In a another embodiment, the abnormality is osteoporosis in which the agonist would activate bone regeneration. In still another embodiment, the abnormality is a blood disorder in which the agonist would activate blood coagulation.

This invention provides a method of treating an abnormality in a subject wherein the abnormality is alleviated by decreasing the activity of a mammalian LPA receptor which comprises administering to the subject an amount of compound which is a mammalian LPA receptor antagonist effective to treat the abnormality.

In a further embodiment, the abnormality is cancer in which the antagonist preferably reduces or prevents tumors, platelet aggregation in which the antagonist preferably acts as an anti-coagulant, vascular restenosis, arthritis in which the antagonist acts as an anti-inflammatory, and cosmetic uses in which the antagonist preferably prevents abnormal growths or scarring.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

Cloning and sequencing a novel mammalian LPA receptor
Isolation and sequencing of a partial mammalian LPA receptor A human lymphocyte genomic phage library (Stratagene, LaJolla, Calif.) was screened using degenerate transmembrane (TM) oligonucleotide probes, from TM 2 and 7, derived from the human Y1 (Larhammar et al., 1992; GenBank accession No. Z11504), human Y2 (Gerald et al., 1995; GenBank accession No. U36269), human Y4 (Bard et al., 1995; GenBank accession No. U35232) and human Y5 (Gerald et al., 1996; GenBank accession No. U56079) neuropeptide receptor genes.

The following degenerate oligomers from TM2 were used:

A 5'-(A/G)(C/T)I(A/G)(C/T)(A/C)AAC(A/C/G/T)Ti C/T)TiATiG(A/C/G/T)(G/C)AA(C/T)CT(G/T)(G/T)C (C/T)(G/T)Ti(G/T)C(A/T)GA(C/T)(A/C/G/T)Ti(C/T) TC-3';

B 5'-GA(C/T)(A/C/G/T)Ti(C/T)Ti(A/G)T(G/T)I(A/C/G/ T) (G/C)(A/C)(C/T)I(A/C/G/T)TiTG(C/T)(C/T)(A/C/ G/T)iCCi(C/T)TiACii(C/T)I(A/G)(C/T)(G/C)T(A/C) T-3';

C 5'-GT(G/C)ACiAA(C/T)(A/T)T(C/T)(C/T)T(G/C)AT (C/T)G(C/T)(C/T)AA(C/T)CT(G/C)(G/T)C(C/T)(G/ T)T (C/T)(G/T)C(C/T)GA(C/T)CT(G/C)CTC-3'; and D 5'-GA(C/T)CT(G/C)CT(G/C)GT(G/C)(A/G)(A/C)(C/ T)A (C/T)I(A/C)T(G/C)TG(C/T)CT(G/C)CC(A/T)TT (C/T)AC i(C/T)T(G/C)GC(G/C)TAT-3'.

The sequences of the preceding oligomers may be represented as follows:

A 5'-RYNRYMAACNTNYTNATNGNSAAYCTKKC-YKTNKCWGAYNTNYTC-3' (Sequence I.D. No. 5);

B 5'-GAYNTNYTNRTKNNSMYNNTNTGYYNNCC-NYTNACNNYNRYSTMT-3' (Sequence I.D. No. 6);

C 5'-GTSACNAAYWTYYTSATYGYYAAYCTSKCY-KTYKCYGAYCTSCTC-3' (Sequence I.D. No. 7); and D 5'-GAYCTSCTSGTSRMYAYNMTSTGYCTSCCW-TTYACNYTSGCSTAT-3' (Sequence I.D. No. 8), respectively.

The following degenerate oligomers from TM7 were used:

E  5'-(A/T/C)(A/C/G/T)I(G/A/C)TiT(G/T)(C/T)CA(C/T)
(A/C/G/T)T(G/C)(A/T/C)(C/T)iG(G/C) (A/C)ATG(G/
A/T)iiTCC(A/T)(G/C)(C/T)T(G/T)(C/T)(G/C) (C/T)
iAA(C/T)CCA-3';

F  5'-ATG(G/A/T)(A/C/G/T)iTCC(A/T)(G/C)(C/T)T(G/
T) (C/T)(G/C)(C/T)(C/T)AA(C/T)CC(A/C)(A/C/G/T)
Ti (A/C/G/T)TiTATGG(G/C)T(G/T)I(A/C)TiAAC-3';

G  5'-AC(C/T)(A/G)T(G/C)TT(C/T)CA(C/T)AT(C/T)AT
(C/T)G(G/C)(C/T)ATG(A/T) (G/T)iTC(C/T)AC(C/T)
T(G/T)(C/T)G(C/T)(C/T)AA(C/T)CCA-3'; and H  5'-ATG(A/T)(G/T)GTC(C/T)TG(C/T)T(G/T)(C/T)CT
(G/C) AA(C/T)CCA(A/C)T(C/T)CT(G/C)TA(C/T)GG
(A/C)T(G/T(C/T)CT(G/C)AAT-3'.

The sequences of the preceding oligomers may be represented as follows:

E  5'-HNNVTNTKYCAYNTSHYNGSMATGDNNTC-CWSYTKYSYNAAYCCA-3' (Sequence I.D. No. 9);

F  5'-ATGDNNTCCWSYTKYSYYAAYCCMNTNNT-NTATGGSTKNMTNAAC-3' (Sequence I.D. No. 10);

G  5'-ACYRTSTTYCAYATYATYGSYATGWKNTCY-ACYTKYGYYAAYCCA-3' (Sequence I.D. No. 11); and H  5'-ATGWKGTCYTGYTKYCTSAAYCCAMTYCT-STAYGGMTKYCTSAAT-3' (Sequence I.D. No. 12).

Degenerate oligomers from TM2 and TM7 were labeled with [$^{32}$P]-ATP using T4 polynucleotide kinase (Boehringer Mannheim). Hybridization was performed at low stringency conditions: 40° C. in a solution containing 5×SSC (1×SSC is 0.15 M sodium chloride, 0.015 M sodium citrate), 1×Denhardt's solution (0.02% polyvinylpyrrolindone, 0.02% Ficoll, 0.02% bovine serum albumin), 7 mM Tris, 7% sodium dodecyl sulfate and 25 µg/ml sonicated salmon sperm DNA. The filters were washed at 40° C. in 0.1×SSC containing 0.5% sodium dodecyl sulfate and exposed at −70° C. to Kodak XAR film in the presence of an intensifying screen. Lambda phage clones hybridizing with the probes were plaque purified and DNA was prepared for Southern blot analysis (Sambrook et al., 1989). A genomic clone hybridizing with the TM2 probes, designated hl18a, was isolated using this method. For subcloning and further Southern blot analysis, the hl18a DNA was cloned into pUC18(Pharmacia, Piscataway, N.J.). Nucleotide sequence analysis was accomplished by the Sanger dideoxy nucleotide chain termination method on denatured double-stranded plasmid templates, using Sequenase (US Biochemical Corp., Cleveland, Ohio).

Isolation and Sequencing of a Full-length Mammalian LPA Receptor

To isolate a full-length hl18a receptor, a human hippocampal library (Gerald, 1995) was screened by polymerase chain reaction (PCR) using primers designed against hl18a DNA (sense primer and reverse primer).

sense primer: 5'-CCCCTCAGGATCTCCTTGGCCAT-3' (Sequence I.D. No. 13)

reverse primer: 5'GCGCTGGACGATGAT-GAGGAAGC-3' (Sequence I.D. No. 14)

1 µl of bacterial stock from each of 37 superpools of 50,000 independent clones was amplified using the Expand Long Template PCR System (Boehringer Mannheim), and the resulting products analyzed by agarose gel electrophoresis. The conditions for PCP were 94° C. for 2 min. and 68° C. for 4 min. for 40 cycles with a 5 min. preincubation at 95° C. and a 10 min. postincubation at 68° C. One positive superpool, H. Hippo. B3, was analyzed further and a single cDNA clone, H. Hippo. 220-74-49, was isolated by sib selection. By PCR, this clone (renamed H. Hippo hl18a) was determined to be in the wrong orientation for expression. To obtain a construct in the correct orientation, an EcoRI fragment of H. Hippo hl18a was ligated into the pEXJ expression vector. Plasmid DNA was prepared and was named #775 (also known as HL-18a). Nucleotide sequence analysis was accomplished by the Sanger dideoxy nucleotide chain termination method on denatured double-stranded plasmid templates, using Sequenase (US Biochemical Corp., Cleveland, Ohio).

Cell Culture

COS-7 cells are grown on 150 mm plates in DMEM with supplements (Dulbecco's Modified Eagle Medium with 10% bovine calf serum, 4 mM glutamine, 100 units/ml penicillin/100 µg/ml streptomycin) at 37° C., 5% $CO_2$. Stock plates of COS-7 cells are trypsinized and split 1:6 every 3–4 days.

Human embryonic kidney 293 cells are grown on 150 mm plates in DMEM with supplements (10% bovine calf serum, 4 mM glutamine, 100 units/ml penicillin/100 µg/ml streptomycin) at 37° C., 5% $CO_2$. Stock plates of 293 cells are trypsinized and split 1:6 every 3–4 days.

Mouse fibroblast LM(tk−) cells are grown on 150 mm plates in D-MEM with supplements (Dulbecco's Modified Eagle Medium with 10% bovine calf serum, 4 mM glutamine, 100 units/ml penicillin/100 µg/ml streptomycin) at 37° C, 5% $CO_2$. Stock plates of LM(tk−) cells are trypsinized and split 1:10 every 3–4 days. Chinese hamster ovary (CHO) cells were grown on 150 mm plates in HAM's F-12 medium with supplements (10% bovine calf serum, 4 mM L-glutamine and 100 units/ml penicillin/100 ug/ml streptomycin) at 37° C., 5% CO2. Stock plates of CHO cells are trypsinized and split 1:8 every 3–4 days.

Mouse embryonic fibroblast NIH-3T3 cells are grown on 150 mm plates in Dulbecco's Modified Eagle Medium (DMEM) with supplements (10% bovine calf serum, 4 mM glutamine, 100 units/ml penicillin/100 µg/ml streptomycin) at 37° C., 5% CO2. Stock plates of NIH-3T3 cells are trypsinized and split 1:15 every 3–4 days.

Sf9 and Sf21 cells are grown in monolayers on 150 mm tissue culture dishes in TMN-FH media supplemented with 10% fetal calf serum, at 27° C., no $CO_2$. High Five insect cells are grown on 150 mm tissue culture dishes in Ex-Cell 400™ medium supplemented with L-Glutamine, also at 27° C., no $CO_2$.

Transfection

Receptors studied may be transiently transfected into COS-7 cells by the DEAE-dextran method, using 1 µg of DNA/$10^6$ cells (Cullen, 1987). In addition, Schneider 2 Drosophila cells may be cotransfected with vectors containing the receptor gene, under control of a promoter which is active in insect cells, and a selectable resistance gene, eg., the G418 resistant neomycin gene, for expression of the polypeptides disclosed herein.

Stable Transfection

DNA encoding the polypeptides disclosed herein may be co-transfected with a G-418 resistant gene into the human embryonic kidney 293 cell line by a calcium phosphate transfection method (Cullen, 1987). Stably transfected cells are selected with G-418.

Membrane Preparations

LM(tk−) cells stably transfected with the DNA encoding the mammalian LPA receptor disclosed herein may be routinely converted from an adherent monolayer to a viable suspension. Adherent cells are harvested with trypsin at the point of confluence, resuspended in a minimal volume of complete DMEM for a cell count, and further diluted to a concentration of $10^6$ cells/ml in suspension media (10% bovine calf serum, 10% 10×Medium 199 (Gibco), 9 mM $NaHCO_3$, 25 mM glucose, 2 mM L-glutamine, 100 units/ml penicillin/100 μg/ml streptomycin, and 0.05% methyl cellulose). Cell suspensions are maintained in a shaking incubator at 37° C., 5% $CO_2$ for 24 hours. Membranes harvested from cells grown in this manner may be stored as large, uniform batches in liquid nitrogen. Alternatively, cells may be returned to adherent cell culture in complete DMEM by distribution into 96-well microtiter plates coated with poly-D-lysine (0.01 mg/ml) followed by incubation at 37° C., 5% $CO_2$ for 24 hours.

Generation of Baculovirus

The coding region of DNA encoding the mammalian LPA receptor disclosed herein may be subcloned into pBlue-BacIII into existing restriction sites, or sites engineered into sequences 5' and 3' to the coding region of the polypeptides. To generate baculovirus, 0.5 μg of viral DNA (BaculoGold) and 3 μg of DNA construct encoding a polypeptide may be co-transfected into $2×10^6$ *Spodoptera frugiperda* insect Sf9 cells by the calcium phosphate co-precipitation method, as outlined in by Pharmingen (in "Baculovirus Expression Vector System: Procedures and Methods Manual"). The cells then are incubated for 5 days at 27° C.

The supernatant of the co-transfection plate may be collected by centrifugation and the recombinant virus plaque purified. The procedure to infect cells with virus, to prepare stocks of virus and to titer the virus stocks are as described in Pharmingen's manual.

Radioligand Binding Assays

Cells may be screened for the presence of endogenous mammalian LPA receptor using radioligand binding or functional assays (described in detail in the following experimental description). Cells with either no or a low level of endogenous LPA receptor present may be transfected with the mammalian LPA receptor.

Transfected cells from culture flasks are scraped into 5 ml of Tris-HCl, 5mM EDTA, pH 7.5, and lysed by sonication. The cell lysates are centrifuged at 1000 rpm for 5 min. at 4° C., and the supernatant is centrifuged at 30,000× g for 20 min. at 4° C. The pellet is suspended in binding buffer (50 mM Tris-HCl, 5 mM $MgSO_4$, 1 mM EDTA at pH 7.5 supplemented with 0.1% BSA, 2 μg/ml aprotinin, 0.5 mg/ml leupeptin, and 10 μg/ml phosphoramidon). Optimal membrane suspension dilutions, defined as the protein concentration required to bind less than 10% of the added radioligand, are added to 96-well polpropylene microtiter plates containing $^3$H-labeled compound, unlabeled compounds, and binding buffer to a final volume of 250 μl. In equilibrium saturation binding assays membrane preparations are incubated in the presence of increasing concentrations of [$^3$H]-labeled compound. The binding affinities of the different compounds are determined in equilibrium competition binding assays, using [$^3$H]-labeled compound in the presence of ten to twelve different concentrations of the displacing ligands. Binding reaction mixtures are incubated for 1 hr at 30° C., and the reaction stopped by filtration through GF/B filters treated with 0.5% polyethyleneimine, using a cell harvester. Radioactivity may be measured by scintillation counting and data are analyzed by a computerized non-linear regression program. Non-specific binding is defined as the amount of radioactivity remaining after incubation of membrane protein in the presence of unlabeled. Protein concentration may be measured by the Bradford method using Bio-Rad Reagent, with bovine serum albumin as a standard.

Functional Assays

Cells may be screened for the presence of endogenous mammalian LPA receptor using radioligand binding or functional assays (described in detail in the above or following experimental description, respectively). Cells with no or a low level of endogenous LPA receptor present may be transfected with the mammalian LPA receptor for use in the following functional assays.

Cyclic AMP (cAMP) Formation Assay

The receptor-mediated inhibition of cyclic AMP (cAMP) formation may be assayed in transfected cells expressing the mammalian LPA receptors. Cells are plated in 96-well plates and incubated in Dulbecco's phosphate buffered saline (PBS) supplemented with 10 mM HEPES, 5 mM theophylline, 2 μg/ml aprotinin, 0.5 mg/ml leupeptin, and 10 μg/ml phosphoramidon for 20 min at 37° C., in 5% $CO_2$. Test compounds are added and incubated for an additional 10 min at 37° C. The medium is then aspirated and the reaction stopped by the addition of 100 mM HCl. The plates are stored at 4° C. for 15 min, and the cAMP content in the stopping solution measured by radioimmunoassay. Radioactivity may be quantified using a gamma counter equipped with data reduction software.

Arachidonic Acid Release Assay

Stably transfected cells with the mammalian LPA receptor are seeded into 96 well plates and grown for 3 days in HAM's F-12 with supplements. $^3$H-arachidonic acid (specific activity=0.75 μCi/ml) is delivered as a 100 μL aliquot to each well and samples were incubated at 37° C., 5% $CO_2$ for 18 hours. The labeled cells are washed three times with 200 μL HAM's F-12. The wells are then filled with medium (200 μL) and the assay is initiated with the addition of peptides or buffer (22 μL). Cells are incubated for 30 min at 37° C., 5% $CO_2$. Supernatants are transferred to a microtiter plate and evaporated to dryness at 75° C. in a vacuum oven. Samples are then dissolved and resuspended in 25 μL distilled water. Scintillant (300 μL) is added to each well and samples are counted for $^3$H in a Trilux plate reader. Data are analyzed using non-linear regression and statistical techniques available in the GraphPAD Prism package (San Diego, Calif.).

Intracellular Calcium Mobilization Assay

The intracellular free calcium concentration may be measured by microspectroflourometry using the fluorescent indicator dye Fura-2/AM (Bush et al, 1991). Stably transfected cells are seeded onto a 35 mm culture dish containing a glass coverslip insert. Cells are washed with HBS and loaded with 100 μL of Fura-2/AM (10 μM) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques.

Phosphoinositide Metabolism Assay

Cells stably expressing the mammalian LPA receptor cDNA are plated in 96-well plates and grown to confluence. The day before the assay the growth medium is changed to 100 μl of medium containing 1% serum and 0.5 μCi [$^3$H] myo-inositol, and the plates are incubated overnight in a $CO_2$ incubator (5% $CO_2$ at 37° C.). Alternatively, arachidonic acid release may be measured if [$^3$H]arachidonic acid is substituted for the [$^3$H]myoinositol. Immediately before the assay, the medium is removed and replaced by 200 μL of PBS containing 10 mM LiCl, and the cells are equilibrated with the new medium for 20 min. During this interval cells are also equilibrated with the antagonist, added as a 10 μL aliquot of a 20-fold concentrated solution in PBS. The [$^3$H]inositol-phosphates accumulation from inositol phospholipid metabolism may be started by adding 10 μL of a solution containing the agonist. To the first well 10 μL may be added to measure basal accumulation, and 11 different concentrations of agonist are assayed in the following 11 wells of each plate row. All assays are performed in duplicate by repeating the same additions in two consecutive plate rows. The plates are incubated in a $CO_2$ incubator for 1 hr. The reaction may be terminated by adding 15 μL of 50% v/v trichloroacetic acid (TCA), followed by a 40 min. incubation at 4° C. After neutralizing TCA with 40 μL of 1 M Tris, the content of the wells may be transferred to a Multiscreen HV filter plate (Millipore) containing Dowex AG1-X8 (200–400 mesh, formate form). The filter plates are prepared adding 200 μL of Dowex AG1-X8 suspension (50% v/v, water: resin) to each well. The filter plates are placed on a vacuum manifold to wash or elute the resin bed. Each well is washed 2 times with 200 μL of water, followed by 2×200 μL of 5 mM sodium tetraborate/60 mM ammonium formate. The [$^3$H]IPs are eluted into empty 96-well plates with 200 μL of 1.2 M ammonium formate/0.1 formic acid. The content of the wells is added to 3 ml of scintillation cocktail, and the radioactivity is determined by liquid scintillation counting.

GTPγS Functional Assay

Membranes from cells transfected with the mammalian LPA receptors are suspended in assay buffer (50 mM Tris, 100 mM NaCl, 5 mM $MgCl_2$, pH 7.4) supplemented with 0.1% BSA, 0.1% bacitracin and 10 μM GDP. Membranes are incubated on ice for 20 minutes, transferred to a 96-well Millipore microtiter GF/C filter plate and mixed with GTPγ$^{35}$S (e.g., 250,000 cpm/sample, specific activity ~1000 Ci/mmol) plus or minus GTPγS (final concentration=100 μM). Final membrane protein concentration≈90 μg/ml. Samples are incubated in the presence or absence of test compound (final concentration=1 μM) for 30 min. at room temperature, then filtered on a Millipore vacuum manifold and washed three times with cold assay buffer. Samples collected in the filter plate are treated with scintillant and counted for $^{35}$S in a Trilux (Wallac) liquid scintillation counter. It is expected that optimal results are obtained when the mammalian LPA receptor membrane preparation is derived from an appropriately engineered heterologous expression system, i.e., an expression system resulting in high levels of expression of the mammalian LPA receptor and/or expressing G-proteins having high turnover rates (for the exchange of GDP for GTP). GTP$_γ$S assays are well-known in the art, and it is expected that variations on the method described above, such as are described by e.g., Tian et al. (1994) or Lazareno and Birdsall (1993), may be used by one of ordinary skill in the art.

MAP Kinase Assay MAP kinase (mitogen activated kinase) may be monitored to evaluate receptor activation. MAP kinase is activated by multiple pathways in the cell. A primary mode of activation involves the ras/raf/MEK/MAP kinase pathway. Growth factor (tyrosine kinase) receptors feed into this pathway via SHC/Grb-2/SOS/ras. Gi coupled receptors are also known to activate ras and subsequently produce an activation of MAP kinase. Receptors that activate phospholipase C (Gq and G11) produce diacylglycerol (DAG) as a consequence of phosphatidyl inositol hydrolysis. DAG activates protein kinase C which in turn phosphorylates MAP kinase.

MAP kinase activation can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the mitogen and then extracted with Laemmli buffer. The soluble fraction is applied to an SDS-PAGE gel and proteins are transferred electrophoretically to nitrocellulose or Immobilon. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the mitogen and a soluble extract is prepared. The extract is incubated at 30° C. for 10 min with gamma-32-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatrography paper is washed and counted for $^{32}$P in a liquid scintillation counter. Alternatively, the cell extract is incubated with gamma-32-ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then by aspirated through the filter, which retains the phosphorylated myelin basic protein. The filter is washed and counted for $^{32}$P by liquid scintillation counting.

Cell Proliferation Assay

Receptor activation of a G protein coupled receptor may lead to a mitogenic or proliferative response which can be monitored via $^3$H-thymidine uptake. When cultured cells are incubated with $^3$H-thymidine, the thymidine translocates into the nuclei where it is phosphorylated to thymidine triphosphate. The nucleotide triphosphate is then incorporated into the cellular DNA at a rate that is proportional to the rate of cell growth. Typically, cells are grown in culture for 1–3 days. Cells are forced into quiescence by the removal of serum for 24 hrs. A mitogenic agent is then added to the media. 24 hrs later, the cells are incubated with $^3$H-thymidine at specific activities ranging from 1 to 10 uCi/ml for 2–6 hrs. Harvesting procedures may involve trypsinization and trapping of cells by filtration over GF/C filters with or without a prior incubation in TCA to extract soluble thymidine. The filters are processed with scintillant and counted for $^3$H by liquid scintillation counting. Alternatively, adherant cells are fixed in MeOH or TCA, washed in water, and solubilized in 0.05% deoxycholate/0.1 N NaOH. The soluble extract is transferred to scintillation vials and counted for $^3$H by liquid scintillation counting.

It is to be understood that the cell lines described herein are merely illustrative of the methods used to evaluate the binding and function of the mammalian LPA receptors of the present invention, and that other suitable cells may be used in the assays described herein.

Methods for Recording Currents in Xenopus Oocytes

Female Xenopus laevis (Xenopus-1, Ann Arbor, Mich.) are anesthetized in 0.2% tricain (3-aminobenzoic acid ethyl ester, Sigma Chemical Corp.) and a portion of ovary is removed using aseptic technique (Quick and Lester, 1994). Oocytes are defolliculated using 3 mg/ml collagenase (Worthington Biochemical Corp., Freehold, N.J.) in a solution containing 87.5 mM NaCl, 2 mM KCl, 2 mM $MgCl_2$ and 5 mM HEPES, pH 7.5. Oocytes are injected (Nanoject, Drummond Scientific, Broomall, Pa.) with 2–2.5 ng cRNA transcribed from mammalian cDNA using T7 polymerase (Ambion). Alternatively, mRNA may be translated from a template generated by PCR, incorporating a T7 promoter and a poly $A^+$ tail. After injection of mRNA, oocytes are incubated at 16° on a rotating platform for 3–8 days.

Dual electrode voltage clamp ("GeneClamp", Axon Instruments Inc., Foster City, Calif.) is performed using 3 M KCl-filled glass microelectrodes having resistances of 1–3 Mohms. Unless otherwise specified, oocytes are voltage clamped at a holding potential of −80 mV. During recordings, oocytes are bathed in continuously flowing (2–5 ml/min) medium containing 96 mM NaCl, 2 mM KCl, 2 mM $CaCl_2$, 2 mM $MgCl_2$, and 5 mM HEPES, pH 7.5 ("ND96"). Drugs are applied by switching from a series of gravity fed perfusion lines.

Heterologous expression of GPCRs in Xenopus oocytes has been widely used to determine the identity of signaling pathways activated by agonist stimulation (Gundersen et al., 1983; Takahashi et al., 1987). Activation of the phospholipase C (PLC) pathway is assayed by applying test compound in ND96 solution to oocytes previously injected with mRNA for the mammalian LPA receptor and observing inward currents at a holding potential of −80 mV. The appearance of currents that reverse at −25 mV and display other properties of the $Ca^{++}$-activated $Cl^-$(chloride) channel is indicative of mammalian LPA receptor-activation of PLC and release of IP3 and intracellular $Ca^{++}$. Such activity is exhibited by GPCRs that couple to $G_q$.

Measurement of G-protein inwardly rectifying $K^+$ (potassium) channel (GIRK) activity is monitored in oocytes that have been co-injected with mRNAs encoding the mammalian LPA receptor, GIRK1, and GIRK4. The two GIRK gene products co-assemble to form a G-protein activated potassium channel known to be activated (i.e., stimulated) by a number of GPCRs that couple to $G_i$ or $G_o$ (Kubo et al., 1993; Dascal et al., 1993). Genes encoding GIRK1 and GIRK4 are obtained by PCR using the published sequences (Kubo et al., 1993; Dascal et al., 1993; Krapivinsky et al., 1995 and 1995b) to derive appropriate 5' and 3' primers. Human heart cDNA was used as template together with the primers 5'-CGCGGATCCATTATGTCTGCACTCCGAAGGAA-ATTTG-3' (Seq. I.D. No. 15) and 5'-CGCGAATTCTTATGTGAAGCGATCAGAGTTCA-TTTTTC-3' (Seq. I.D. No. 16) for GIRK1 and 5'-GCGGGATCCGCTATGGCTGGTGATTCTAGGAA-TG-3' (Seq. I.D. No. 17) and 5'-CCGGAATTCCCCTCACACCGAGCCCCTGG-3' (Seq. I.D. No. 18) for GIRK4.

In each primer pair, the upstream primer contained a BamHI site and the downstream primer contained an EcoRI site to facilitate cloning of the PCR product into pcDNA1-Amp (Invitrogen). mRNAs are prepared from separate DNA plasmids containing the complete coding regions of the mammalian LPA receptor, GIRK1, and GIRK4. Plasmids are linearized and transcribed using the T7 polymerase ("Message Machine", Ambion). Oocytes (prepared as described above) are injected with mammalian LPA receptor mRNA (2–2.5 ng) plus the two GIRK subunits (2 ng each). After injection of mRNA, oocytes are incubated at 16° on a rotating platform for 3–8 days.

Dual electrode voltage clamp is performed as described above, except that oocytes are bathed in continuously flowing (2–5 ml/min) medium containing elevated $K^+$ containing 49 mM KCl, 49 mM NaCl, 2 mM CaCl, 2 mM $MgCl_2$, and 5 mM HEPES, pH 7.5 ("hK"). The oocytes are tested for responsivity to agonists and antagonists by measuring $K^+$ currents in elevated $K^+$ solution (hK). Activation of inwardly rectifying currents that are sensitive to 300 $\mu$M $Ba^{++}$ signifies the mammalian LPA receptor coupling to a $G_i$ or $G_o$ pathway in the oocytes.

Experimental Results

A human genomic lymphocyte library was screened, under reduced stringency conditions, with degenerate oligonucleotide probes directed to the second and seventh transmembrane regions of the human Y1 (Larhammar, D. et al., 1992; GenBank accession No. Z11504), human Y2 (Gerald et al., 1995; GenBank accession No. U36269), human Y4 (Bard et al., 1995; GenBank accession No. U35232) and human Y5 (Gerald et al., 1996; GenBank accession No. U56079) neuropeptide receptor genes. Positively-hybridizing clones were isolated, plaque-purified, and characterized by Southern blot analysis and sequencing. One clone, hl18a, contained an 800 bp HindIII/HindII fragment which hybridized with the rat Y2-derived oligonucleotide probes and was subsequently subcloned into a pUC vector. This clone was a partial gene fragment, encoding a starting methionine through the 3' end of a putative TM3, with the possibility of an immediate downstream intron.

In order to obtain a full-length clone, a human hippocampal library was screened by PCR using primers directed against hl18a. One positive superpool, H.Hippo.B3, was successfully subdivided until a single clone, H.Hippo. 220-74-49, was isolated. As this clone was in the wrong orientation for expression, the insert was removed by restriction digestion and re-ligated into the expression vector pEXJ in the correct orientation. The largest open reading frame in this construct, #775 (also known as HL-18a), contains 1299 nucleotides, which is predicted to encode a protein of 433 amino acids. Using a downstream methionine, with a better Kozak consensus site (Kozak, 1991), results in an open frame of 1116 nucleotides and is predicted to encode a protein of 372 amino acids. Hydropathy analysis of the protein is consistent with a putative topography of seven transmembrane domains, indicative of the G protein-coupled receptor family.

A comparison of nucleotide and peptide sequences of clone #775 (HL-18a) with sequences contained in the Genbank/EMBL databases reveals that the clone is most related to Xenopus laevis high-affinity lysophosphatidic acid receptor (GenBank accession # U76385) (Guo, et al., 1996). There is a 67% nucleotide identity and 70% amino acid identity between clone #775 (HL-18a) and the Xenopus laevis high-affinity lysophosphatidic acid receptor.

REFERENCES

Bard, J. A., Walker, M. W., Branchek, T. A., and Weinshank, R. L. (1995) J. Biol. Chem. 270(45):26762–26765.

Burns, C. M., Chu, H., Rueter, S. M., Sanders-Bush, E., and Erneson, R. B. (1996) Neuroscience Abstracts 385.9.

Chu, H., Burns, C., Canton, H., Erneson, R. B., and Sanders-Bush, E. (1996) Neuroscience Abstracts 385.10.

Cullen, B. (1987) Methods Enzymol. 152:685–704.

Coleman, A. (1984) Transcription and Translation: A Practical Approach (B. D. Hanes, S. J. Higgins, eds., pp 271–302, IRL Press, Oxford, 1984).

Dascal, N., Schreibmayer, W., Lim, N. F., Wang, W., Chavkin, C., DiMagno, L., Labarca, C., Kieffer, B. L., Gaveriaux-Ruff, C., Trollinger, D., Lester, H. A., Davidson, N. (1993) Proc. Natl. Acad. Sci. USA 90:10235–10239.

Gerald, C., Walker, M. W., Vaysse, P. J.-J., He, C., Branchek, T. A., and Weinshank, R. L. (1995) J. Biol. Chem. 270(45):26758–26761.

Gerald, C., Walker, M. W., Criscione, L., Gustafson, E. L., Barzyl-Hartmann, C., Smith, K. E., Vaysse, P., Durkin, M. M., Laz, T. M., Linemeyer, D. L., Schaffhauser, A. O., Whitebread, S., Hofbauer, K. G., Taber, R. I., Branchek, T. A., and Weinshank, P. L. (1996) Nature 382:168–171.

Gundersen, C. B., Miledi, P., Parker, I. (1983) Proc. R. Soc. London Ser. B 219:103–109.

Guo, Z., Liliom, K., Fischer, D. J., Bathurst, I., Tomei, L. D., Kiefer, M. C., and Tigyi, G. (1996) Proc. Natl. Acad. Sci. USA 93:14367–14372.

Jalink, K., Hordijk, P. L., and Moolenaar, W. H. (1994) Biochim. Biophys. Acta. 1198:185–196.

Jalink, K., Eichholtz, T., Postma, F. R. van Corven, F. J., and Moolenaar, W. H. (1993) Cell Growth and Differ. 4:247–255.

Kozak, M. (1991) J. Biol. Chem. 266:19867–19870.

Krapivinsky, G., Gordon, E. A., Wickman, B., Velimirovic, B., Krapivinsky, L., Clapham, D. E. (1995) Nature 374:135–141.

Krapivinsky, G., Krapivinsky, L., Velimirovic, B., Wickman, K., Navarro, B., Clapman, D. E., (1995b) J. Biol. Chem. 270:28777–28779.

Kubo, Y., Peuveny, E., Slesinger, P. A., Jan, Y. N. and Jan, L. Y. (1993) Nature 364:802–806.

Lazareno, S. and Birdsall, N. (1993) Br. J. Pharmacol. 109:1120–1127.

Larhammar, D., Blomqvist, A. G., Yee, F., Jazin, E., Yoo, H., Wahlestedt, C. (1992) J. Biol. Chem. 267:10935–10938.

Masu, Y. et al. (1994) Nature 329:21583–21586.

Moolenaar, W. H. (1994) Trends Cell Biol. 4:213–219.

Moolenaar, W. H. (1995) J. Biol. Chem. 270:12949–12952.

Piazza, G. A., Ritter, J. L., and Baracka, C. A. (1995) Exp. Cell Res. 216:51–64.

Quick, M. W. and Lester, H. A. (1994) Meth. Neurosci. 19:261–279.

Sambrook, J., Fritsch, E. F., and Maniatis, T. (1989) Molecular cloning: A laboratory manual (Cold Spring Harbor Press, Cold Spring Harbor, N.Y.), 2nd Ed.

Takahashi, T., Neher, E., and Sakmann, B. (1987) Proc. Natl. Acad. Sci. USA 84:5063–6067.

Thomson, F. J., Perkins, L., Ahern, D., and Clark, M. (1994) Mol. Pharmacol. 45:718–728

Tian, W. N., Duzic, E., Lanier, S., and Deth, R. C. (1994) Mol. Pharmacol. 45:524–531.

Tigyi, G., Dyer, D. L., and Mildi, P. (1994) Proc. Natl. Acad. Sci. U.S.A. 91:1908–1912.

Tigyi, G. and Miledi, R. (1992) J. Biol. Chem. 267:21360–21367.

Tokumura, A., Iimori, M., Nishioka, Y., Kitahara, M., Sakashita, M., and Tanaka, S. (1994) Am. J. Physiolo. 267: C204–C210.

Van Corven, E. J., Groenink, A., Jalink, K., Eichholtz, T., and Moolenaar, W. H. (1989) Cell 59:45–54.

---

What is claimed is:

1. An isolated nucleic acid encoding a human LPA receptor, wherein the human LPA receptor has an amino acid sequence identical to the amino acid sequence of the human LPA receptor encoded by the plasmid HL-18a (ATCC Accession No. 209448).

2. An isolated nucleic acid encoding a human LPA receptor, wherein the human LPA receptor comprises an amino acid sequence identical to the amino acid sequence shown in FIG. 3 (Seq. I.D. No. 3).

3. The nucleic acid of claim 1 or 2, wherein the nucleic acid is DNA.

4. The DNA of claim 3, wherein the DNA is cDNA.

5. The nucleic acid of claim 1 or 2, wherein the nucleic acid is RNA.

6. A vector comprising the nucleic acid of claim 1 or 2.

7. A vector of claim 6 adapted for expression in a bacterial cell which comprises the regulatory elements necessary for expression of the nucleic acid in the bacterial cell operatively linked to the nucleic acid encoding the human LPA receptor so as to permit expression thereof.

8. A vector of claim 6 adapted for expression in an amphibian cell which comprises the regulatory elements necessary for expression of the nucleic acid in the amphibian cell operatively linked to the nucleic acid encoding the human LPA receptor so as to permit expression thereof.

9. A vector of claim 6 adapted for expression in a yeast cell which comprises the regulatory elements necessary for expression of the nucleic acid in the yeast cell operatively linked to the nucleic acid encoding the human LPA receptor so as to permit expression thereof.

10. A vector of claim 6 adapted for expression in an insect cell which comprises the regulatory elements necessary for expression of the nucleic acid in the insect cell operatively linked to the nucleic acid encoding the human LPA receptor so as to permit expression thereof.

11. A vector of claim 10 which is a baculovirus.

12. An insect cell comprising the vector of claim 10.

13. An insect cell of claim 12, wherein the insect cell is an Sf9 cell, an Sf21 cell or a HighFive cell.

14. A vector of claim 6 adapted for expression in a mammalian cell which comprises the regulatory elements necessary for expression of the nucleic acid in the mammalian cell operatively linked to the nucleic acid encoding the human LPA receptor so as to permit expression thereof.

15. A vector of claim 6, wherein the vector is a plasmid.

16. A plasmid of claim 15, wherein the plasmid is designated HL-18a (ATCC Accession No. 209448).

17. A cell comprising the vector of claim 6.

18. A cell of claim 17, wherein the cell is a non-mammalian cell.

19. A cell of claim 18, wherein the non-mammalian cell is a Xenopus oocyte cell or a Xenopus melanophore cell.

20. A cell of claim 17, wherein the cell is a mammalian cell.

21. A mammalian cell of claim 20, wherein the cell is a COS-7 cell, a 293 human embryonic kidney cell, a NIH-3T3 cell, a LM(tk−) cell, a mouse Y1 cell, or a CHO cell.

* * * * *

SEQUENCE LISTING

<160> NUMBER OF SEQ ID NOS: 18

<210> SEQ ID NO 1
<211> LENGTH: 1755
<212> TYPE: DNA
<213> ORGANISM: Homo sapiens

<400> SEQUENCE: 1

```
ggaattctag aaacacctgt aaagcttaaa cgcgtgcttt cttcaacgcg tttggaaact      60
ctaaccccct tctcttttgt acttttgctt gctgtccact acagagggtc caagcacgaa     120
gctgtgcaca gagtcgctct ccacagagat gcttaggatg tgatccatga atcgcaaatc     180
ccagctagtg ctcacaaaga cggacatttc tccccaagac cattccagtg ccccagaggt     240
ccacagacat ccaggaagat gcagccagca gacaaagaat ggcagccacc caagtgctga     300
ggggagccct cccggccatt tctgtcccag ctccaagggt ctctccacga tggcctgcaa     360
cagcacgtcc cttgaggctt acacatacct gctgctgaac accagcaacg cctcagactc     420
ggggtccacc cagttgcccg cacccctcag gatctccttg gccatagtga tgctgctgat     480
gaccgtggtg gggttcctgg gcaacactgt ggtctgcatc atcgtgtacc agaggccggc     540
tatgcgctcg gccatcaacc tgctgctggc caccctggcc ttctccgaca tcatgctgtc     600
cctctgctgc atgcccttca ccgccgtcac cctcatcacc gtgcgctggc actttgggga     660
ccacttctgc cgcctctcag ccacgctcta ctggttttt gtcctggagg gcgtggccat     720
cctgctcatc atcagcgtgg accgcttcct catcatcgtc cagcgccagg acaagctgaa     780
cccgcgcagg gccaaggtga tcatcgcggt ctcctgggtg ctgtccttct gcatcgcggg     840
```

-continued

| | |
|---|---|
| gccctcgctc acgggctgga cgctggtgga ggtgccggcg cgggcccac agtgcgtgct | 900 |
| gggctacacg gagctccccg ctgaccgcgc ctacgtggtc accttggtgg tggccgtgtt | 960 |
| cttcgcgccc tttggcgtca tgctgtgcgc ctacatgtgc atcctcaaca cggtccgcaa | 1020 |
| gaaggccgtg cgcgtgcaca accagtcgga cagcctggac ctgcggcagc tcaccagggc | 1080 |
| gggcctgcgg cgcctgcagc ggcagcaaca ggtcagcgtg gacttgagct tcaagaccaa | 1140 |
| ggccttcacc accatcctga tcctcttcgt gggcttctcc ctctgctggc tgccccactc | 1200 |
| cgtctacagc ctcctgtctg tgtttagcca gcgcttttac tgcggttcct ccttctacgc | 1260 |
| caccagcacc tgcgtcctgt ggctcagtta cctcaagtcc gtcttcaacc ccatcgtcta | 1320 |
| ctgctggaga atcaaaaaat ccgcgaggc ctgcatagag ttgctgcccc agaccttcca | 1380 |
| aatcctcccc aaagtgcctg agcggatccg aaggagaatc cagccaagca cagtctacgt | 1440 |
| gtgcaatgaa aaccagtctg cggtttaggg ggtcaggggg ccacagagaa ggggcagctg | 1500 |
| agccccagtc ccagggtgga tctgtcctgc tctgttccct ggcatgttgg tcatagtctg | 1560 |
| cactttgtgg tggcaattta agcacaaagg tactcatttg taatcagatg agctgcagct | 1620 |
| cccaaatttc aaattttggc acgatgaatt attttttgttt ctctttgcag agagccaaat | 1680 |
| atggggctga tgggaactgc aacgtcatta agtcaaaaat ggagtgggct ggggagtgca | 1740 |
| gaagttgggc agaaa | 1755 |

<210> SEQ ID NO 2
<211> LENGTH: 1119
<212> TYPE: DNA
<213> ORGANISM: Homo sapiens

<400> SEQUENCE: 2

| | |
|---|---|
| atggcctgca acagcacgtc ccttgaggct tacacatacc tgctgctgaa caccagcaac | 60 |
| gcctcagact cggggtccac ccagttgccc gcacccctca ggatctcctt ggccatagtg | 120 |
| atgctgctga tgaccgtggt ggggttcctg gcaacactg tggtctgcat catcgtgtac | 180 |
| cagaggccgc ctatgcgctc ggccatcaac ctgctgctgg ccaccctggc cttctccgac | 240 |
| atcatgctgt ccctctgctg catgcccttc accgccgtca ccctcatcac cgtgcgctgg | 300 |
| cactttgggg accacttctg ccgcctctca gccacgctct actggttttt tgtcctggag | 360 |
| ggcgtggcca tcctgctcat catcagcgtg gaccgcttcc tcatcatcgt ccagcgccag | 420 |
| gacaagctga acccgcgcag ggccaaggtg atcatcgcgg tctcctgggt gctgtccttc | 480 |
| tgcatcgcgg ggcctcgct cacgggctgg acgctggtgg aggtgccggc gcgggcccca | 540 |
| cagtgcgtgc tgggctacac ggagctcccc gctgaccgcg cctacgtggt caccttggtg | 600 |
| gtggccgtgt tcttcgcgcc ctttggcgtc atgctgtgcg cctacatgtg catcctcaac | 660 |
| acggtccgca gaaggccgt gcgcgtgcac aaccagtcgg acagcctgga cctgcggcag | 720 |
| ctcaccaggg cgggcctgcg cgcctgcag cggcagcaac aggtcagcgt ggacttgagc | 780 |
| ttcaagacca aggccttcac caccatcctg atcctcttcg tgggcttctc cctctgctgg | 840 |
| ctgccccact ccgtctacag cctcctgtct gtgtttagcc agcgcttta ctgcggttcc | 900 |
| tccttctacg ccaccagcac ctgcgtcctg tggctcagtt acctcaagtc cgtcttcaac | 960 |
| cccatcgtct actgctggag aatcaaaaaa ttccgcgagg cctgcataga gttgctgccc | 1020 |
| cagaccttcc aaatcctccc caaagtgcct gagcggatcc gaaggagaat ccagccaagc | 1080 |
| acagtctacg tgtgcaatga aaaccagtct gcggtttag | 1119 |

```
<210> SEQ ID NO 3
<211> LENGTH: 372
<212> TYPE: PRT
<213> ORGANISM: Homo sapiens

<400> SEQUENCE: 3

Met Ala Cys Asn Ser Thr Ser Leu Glu Ala Tyr Thr Tyr Leu Leu Leu
 1               5                   10                  15

Asn Thr Ser Asn Ala Ser Asp Ser Gly Ser Thr Gln Leu Pro Ala Pro
                20                  25                  30

Leu Arg Ile Ser Leu Ala Ile Val Met Leu Leu Met Thr Val Val Gly
            35                  40                  45

Phe Leu Gly Asn Thr Val Val Cys Ile Ile Val Tyr Gln Arg Pro Ala
 50                  55                  60

Met Arg Ser Ala Ile Asn Leu Leu Leu Ala Thr Leu Ala Phe Ser Asp
 65                  70                  75                  80

Ile Met Leu Ser Leu Cys Cys Met Pro Phe Thr Ala Val Thr Leu Ile
                85                  90                  95

Thr Val Arg Trp His Phe Gly Asp His Phe Cys Arg Leu Ser Ala Thr
            100                 105                 110

Leu Tyr Trp Phe Phe Val Leu Glu Gly Val Ala Ile Leu Leu Ile Ile
        115                 120                 125

Ser Val Asp Arg Phe Leu Ile Ile Val Gln Arg Gln Asp Lys Leu Asn
130                 135                 140

Pro Arg Arg Ala Lys Val Ile Ile Ala Val Ser Trp Val Leu Ser Phe
145                 150                 155                 160

Cys Ile Ala Gly Pro Ser Leu Thr Gly Trp Thr Leu Val Glu Val Pro
                165                 170                 175

Ala Arg Ala Pro Gln Cys Val Leu Gly Tyr Thr Glu Leu Pro Ala Asp
            180                 185                 190

Arg Ala Tyr Val Val Thr Leu Val Ala Val Phe Phe Ala Pro Phe
        195                 200                 205

Gly Val Met Leu Cys Ala Tyr Met Cys Ile Leu Asn Thr Val Arg Lys
    210                 215                 220

Lys Ala Val Arg Val His Asn Gln Ser Asp Ser Leu Asp Leu Arg Gln
225                 230                 235                 240

Leu Thr Arg Ala Gly Leu Arg Arg Leu Gln Arg Gln Gln Val Ser
                245                 250                 255

Val Asp Leu Ser Phe Lys Thr Lys Ala Phe Thr Thr Ile Leu Ile Leu
                260                 265                 270

Phe Val Gly Phe Ser Leu Cys Trp Leu Pro His Ser Val Tyr Ser Leu
            275                 280                 285

Leu Ser Val Phe Ser Gln Arg Phe Tyr Cys Gly Ser Ser Phe Tyr Ala
        290                 295                 300

Thr Ser Thr Cys Val Leu Trp Leu Ser Tyr Leu Lys Ser Val Phe Asn
305                 310                 315                 320

Pro Ile Val Tyr Cys Trp Arg Ile Lys Lys Phe Arg Glu Ala Cys Ile
                325                 330                 335

Glu Leu Leu Pro Gln Thr Phe Gln Ile Leu Pro Lys Val Pro Glu Arg
            340                 345                 350

Ile Arg Arg Arg Ile Gln Pro Ser Thr Val Tyr Val Cys Asn Glu Asn
        355                 360                 365

Gln Ser Ala Val
    370
```

<210> SEQ ID NO 4
<211> LENGTH: 1119
<212> TYPE: DNA
<213> ORGANISM: Xenopus

<400> SEQUENCE: 4

| | | | | | |
|---|---|---|---|---|---|
| atgggctgca | ataatactgc | cctagacaat | tgcatgcttc | ccaatctcag | cattgctact | 60 |
| gctcctctag | acttgaggtt | tgcattttcc | accccactca | ggatgttgtt | ggcaataata | 120 |
| atgatactga | tgattgctat | tgcttttttg | ggcaatgcaa | tagtttgcct | tattgtttat | 180 |
| cagaagccag | ccatgcgttc | agcaatcaat | cttctcctag | caacactggc | attctctgac | 240 |
| atcatgttgt | ccctttttctg | tatgccctt | accgcagtaa | caataataac | tgggagctgg | 300 |
| ctctttggaa | ctcagttttg | ccagatatca | gccatgctgt | actggttttt | tgtgttagaa | 360 |
| ggcgtggcca | ttctacttat | catcagcgtg | gatcgtttcc | ttattattgt | acagaggcag | 420 |
| gacaaactga | acccacatcg | ggccaagatc | atgattgctg | cttcttgggt | actgtctttt | 480 |
| tgtatctctt | taccgtcggt | ggttgggtgg | acgttagtgg | aggtgcctac | acgtgctcca | 540 |
| cagtgtgttc | tcggttatac | agaatttct | gctgacagag | tttatgcagt | catgctcata | 600 |
| gtagcagtct | tcttcattcc | attcagtgta | atgttgtact | cgtatttgtg | tatcctgaac | 660 |
| accgttagaa | gaaatgctgt | cagaattcac | actcatgccg | acagcttgtg | tctcagccaa | 720 |
| gtaagcaaat | tgggacttat | gggacttcag | aggccacacc | aaatgaatgt | ggacatgagt | 780 |
| ttcaaaacca | gggccttcac | cactattttg | attctcttca | ttgggttttc | actctgctgg | 840 |
| cttcctcact | cagtattcag | cttactttca | gtattcagca | ggacattta | ctacagctct | 900 |
| tcattttaca | gcatcagcac | gtgtaccttg | tggctcactt | acctgaagtc | tgtcttcaac | 960 |
| cctgttatat | attgctggag | gatcaagaag | ttccgtgagg | cctgtctgga | gttcatgccc | 1020 |
| aaaacattta | agatccttcc | aaatgtacga | ggaaggacaa | gacggcggat | tcgtccaagc | 1080 |
| acaatttatg | tgtgtgggga | acatcagtca | gctgtttaa | | | 1119 |

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: oligonucleotide probe
<220> FEATURE:
<223> OTHER INFORMATION: n = A/C/T/G or I (inosine)

<400> SEQUENCE: 5
rynrymaacn tnytnatngn saayctkkcy ktnkcwgayn tnytc                45

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: oligonucleotide probe
<220> FEATURE:
<223> OTHER INFORMATION: n = A/C/T/G or I (inosine)

<400> SEQUENCE: 6
gayntnytnr tknnsmynnt ntgyynnccn ytnacnnynr ystmt                45

<210> SEQ ID NO 7
<211> LENGTH: 45

```
<212> TYPE: DNA
<213> ORGANISM: Artificial Sequence
<220> FEATURE:
<223> OTHER INFORMATION: Description of Artificial Sequence:
      oligonucleotide probe
<220> FEATURE:
<223> OTHER INFORMATION: n = A/C/T/G or I (inosine)

<400> SEQUENCE: 7
gtsacnaayw tyytsatygy yaayctskcy ktykcygayc tsctc            45

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence:
      oligonucleotide probe
<220> FEATURE:
<223> OTHER INFORMATION: n = A/C/T/G or I (inosine)

<400> SEQUENCE: 8
gayctsctsg tsrmyaynmt stgyctsccw ttyacnytsg cstat            45

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence:
      oligonucleotide probe
<220> FEATURE:
<223> OTHER INFORMATION: n = A/C/T/G or I (inosine)

<400> SEQUENCE: 9
hnnvtntkyc ayntshyngs matgdnntcc wsytkysyna aycca            45

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence:
      oligonucleotide probe
<220> FEATURE:
<223> OTHER INFORMATION: n = A/C/T/G or I (inosine)

<400> SEQUENCE: 10
atgdnntccw sytkysyyaa yccmntnntn tatggstknm tnaac            45

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence:
      oligonucleotide probe
<220> FEATURE:
<223> OTHER INFORMATION: n = I (inosine)

<400> SEQUENCE: 11
acyrtsttyc ayatyatygs yatgwkntcy acytkygyya aycca            45

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence:
``` oligonucleotide probe

<400> SEQUENCE: 12
atgwkgtcyt gytkyctsaa yccamtycts tayggmtkyc tsaat     45

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 13
cccctcagga tctccttggc cat     23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 14
gcgctggacg atgatgagga agc     23

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 15
cgcggatcca ttatgtctgc actccgaagg aaatttg     37

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 16
cgcgaattct tatgtgaagc gatcagagtt catttttc     38

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 17
gcgggatccg ctatggctgg tgattctagg aatg     34

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 18
ccggaattcc cctcacaccg agccctgg     29